(12) United States Patent
Llatas et al.

(10) Patent No.: US 6,410,768 B1
(45) Date of Patent: Jun. 25, 2002

(54) DIIMINO COMPOUNDS

(75) Inventors: Luis Mendez Llatas, Mostoles; Antonio Muñoz-Escalona Lafuente, Madrid; Juan Campora Perez, Sevilla; Ernesto Carmona Guzman, Sevilla; Manuel Lopez Reyes, Sevilla, all of (ES)

(73) Assignee: Repsol Quimica S.A., Madrid (ES)

( * ) Notice: Subject to any disclaimer, the term of this patent is extended or adjusted under 35 U.S.C. 154(b) by 2 days.

(21) Appl. No.: 09/804,370

(22) Filed: Mar. 12, 2001

(30) Foreign Application Priority Data

Mar. 13, 2000 (EP) .............................................. 00500040

(51) Int. Cl.$^7$ .................................................. C07F 7/10
(52) U.S. Cl. ........................ 556/424; 556/423; 556/403; 556/404; 549/4; 549/214; 546/14; 548/110; 526/90; 526/126; 526/128; 526/340; 526/352; 502/188; 502/155
(58) Field of Search ................................. 556/424, 423, 556/403, 404; 549/215, 4; 546/14; 548/110; 502/188, 155; 526/90, 126, 128, 348, 352

(56) References Cited

U.S. PATENT DOCUMENTS 3,803,090 A * 4/1974 Reinisch et al. ..... 556/424 UX

\* cited by examiner

*Primary Examiner*—Paul F. Shaver
(74) *Attorney, Agent, or Firm*—Ladas & Parry

(57) ABSTRACT

The present invention is related to diimino compounds of formulae (I) $R^2$—N=C($R^1$)($R^3$)$_n$C($R^1$)=N—$R^2$ and (II) ($R^1$)$_2$C=N—(C$R_2^4$)$_m$—N=C($R^1$)$_2$ functionalized with at least one siloxy group. Said diimino compounds are useful for obtaining a solid catalyst component for polymerizing olefins wherein the diimino compound of formulae (I) or (II) is bonded to a porous inorganic support and to a transition metal selected from groups 8, 9 and 10 of the periodic table. This invention also relates to a process for preparing said diimino compounds of formulae (I) or (II), to a process for obtaining said solid catalyst component comprising the combination of the diimino compound and a porous inorganic support. Further, the invention also relates to the use of said solid catalyst in combination with a cocatalyst to polirnenrze olefins.

15 Claims, No Drawings

DIIMINO COMPOUNDS

FIELD OF THE INVENTION

The present invention relates to a new class of diimino compounds useful as ligands for obtaining late transition metal complexes covalently bonded to an inorganic support.

BACKGROUND OF THE INVENTION

It has been recently discovered that alpha-diimino ligands can be used for synthesizing complexes of late transition metals that are useful as catalyst for polymerizing olefins. For instance WO 96/23010 discloses, with several examples, various types of nickel or palladium diiniine complexes, showing that they can be used for polymerizing a large number of olefins.

In WO 98/27124 and WO 98/30612 2,6-pyridinecarboxaldehydebis(imines) and 2,6-diacylpyridinebis(imines) complexes of iron and cobalt are disclosed for polymerizing ethylene and propylene. WO 99/12981 relates to substituted 2,6 diimino pyridines complexes of Fe[II], Fe[III], Co[I], Co[II], Co[III]), Mn[I], Mn[II], Mn[III], Mn[IV], Ru[II], Ru[III] and Ru[IV].

Immobilizing these complexes on solid supports to enable heterogeneous polymerization process such as those based on gas phase, bulky or slurry processes, is important for their efficient industrial utilization. In particular, some non-supported nickel catalysts give rise to polymer characterized by a high level of branching. The melting points of these polymers are anticipated to be as low as to present problems with reactor operation at typical industrial operating temperatures, especially when heat dissipation by solvents is unavailable, as in continuous gas phase polymerization.

Supported diimino nickel or palladium catalysts are disclosed in WO 96/23010, WO 97/48736, WO 98/56832.

WO 96/23010 discloses supported diimino palladium or nickel catalysts. A process wherein a complex activated with a cocatalyst is adsorbed on silica is exemplified.

WO 97/48736 relates to immobilized catalysts; they are substantially obtained by preparing a precursor solution mixing together the complex with an aluminoxane and adding this precursor solution to a porous support.

In some examples of WO 98/56832 the cocatalyst was supported on an inorganic support and then a diimino complex was added, then the obtained catalyst was prepolymerized.

In these applications the diimino ligand is not functionalized for optimizing the bond between the support and the complex. As a result, in the supported catalyst obtained, the migration of the active species into the homogeneous phase during the polymerization reaction may happen.

Therefore the development of a new ligand class that permits a chemical bond between the carTier and the diimino complex is desirable.

An object of the present invention is a new class of diimino ligands functionalized with a siloxy group.

A further object of the present invention is a solid catalyst component for polymerizing olefins comprising: an inorganic support, a diimino ligand chemically bonded to the support and a transition metal.

In this solid component, chemical bonding to the support provides a firm attach of the catalytic centres to the support, resulting in a heterogeneous catalyst component. The preparation of said catalyst precursor results in no contaminating secondary reaction products, hence the catalyst is fiee from undesired impurities. The catalysts can be used in slurry or gas-phase processes. The catalysts are especially useful for the production of branched polyolefins from a single type of monomer.

SUMMARY OF THE INVENTION

The present invention relates to diimino compounds defined by following formulae:

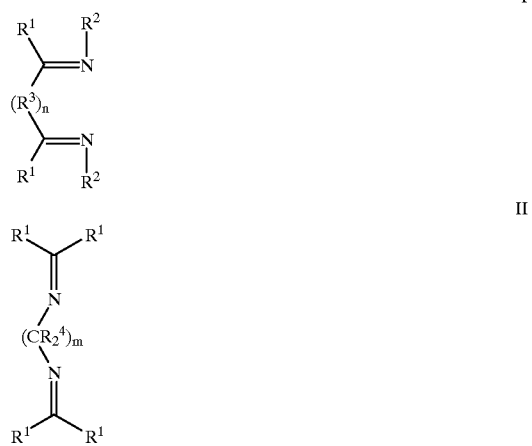

wherein n is 0 or 1; m is 1, 2 or 3;

each $R^1$, equal to or different from each other, is selected from the group consisting of hydrogen, a monovalent aliphatic or aromatic hydrocarbon group, optionally containing heteroatonis of group 14 to 16 of the periodic table of the elements and boron; with the proviso that al least one $R^1$ group is represented by the formula $R^5OSi(R)_3$;

wherein each R is independently selected from the group consisting of: $C_1$–$C_{20}$ allkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, $C_8$–$C_{20}$ alkenylaryl liear or branched; preferably it is methyl, ethyl or propyl;

each $R^5$, equal to or different from each other, is a divalent aliphatic or aromatic hydrocarbon group containing from 1 to 20 carbon atoms, optionally containing from 1 to 5 heteroatoms of groups 14, 15 or 16 of the periodic table of the elements and/or boron;

each $R^2$, equal to or different from each other, is a radical which contains from 1 to 20 carbon atoms; this group optionally contains heteroatoms of group 14 to 16 of the periodic table of the elements and/or boron;

$R^3$ is a divalent aliphatic or aromatic hydrocarbon group containing from 1 to 20 carbon atoms, optionally containing from 1 to 5 heteroatoms of groups 14, 15 and 16 of the periodic table of the elements and/or boron;

$R^4$, equal to or different from each other, is hydrogen or a radical which contains from 1 to 20 carbon atoms; this group optionally contains heteroatoms of group 14 to 16 of the periodic table of the elements and/or boron;

This invention also relates to a process to prepare compounds represented by formula I or II above. Likewise this invention relates to a catalyst component comprising the product of the combination of the dilmino ligand and a porous inorganic support.

Further this invention also relates to the use of the catalyst component in combination with a cocatalyst to polymerize olefins

DETAILED DESCRIPTION OF THE INVENTION

The present invention relates to diimino compounds defined by the following formulae:

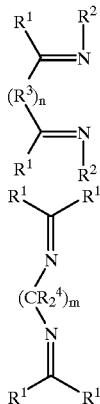

wherein
n is 0 or 1; m is 1, 2 or 3;
each $R^1$, equal to or different from each other, is selected from the group consisting of: hydrogen, a monovalent aliphatic or aromatic hydrocarbon group, optionally containing heteroatoms of group 14 to 16 of the periodic table of the elements and/or boron; with the proviso that al least one $R^1$ group is represented by the formula $R^5OSi(R)_3$;
wherein
each R is independently selected from the group consisting of: $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, $C_8$–$C_{20}$ alkenylaryl linear or branched; preferably it is methyl, ethyl or propyl;
each $R^5$, equal to or different from each other, is a divalent aliphatic or aromatic hydrocarbon group containing from 1 to 20 carbon atoms, optionally containing from 1 to 5 heteroatoms of groups 14, 15 and 16 of the periodic table of the elements and/or boron; preferably it is $CR^6_2(R^7)_aCR^6_2$;
wherein
each $R^6$, equal to or different from each other, is selected from the group consisting of: hydrogen or R; two $R^6$ can also unite to form a ring; $R^7$ is selected from the group consisting of: O, NR, S, $SiR^6_2$, $C_1$–$C_{20}$ alkylidene, $C_3$–$C_{20}$ cycloalkylidene, $C_2$–$C_{20}$ alkenylidene, $C_6$–$C_{20}$ arylidene, $C_7$–$C_{20}$ alkylarylidene, $C_7$–$C_{20}$ arylalkylidene, $C_8$–$C_{20}$ arylalkenylidene, $C_8$–$C_{20}$ alkenylarylidene, optionally containing heteroatoms of group 14 to 16 of the periodic table of the elements, and/or boron; a is 0 or 1;
each $R^2$, equal to or different from each other, is a radical which contains from 1 to 20 carbon atoms; this group optionally contains heteroatoms of group 14 to 16 of the periodic table of the elements and/or boron;
preferably $R^2$ is selected from the group consisting of: $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl alkenylaryl, linear or branched, optionally substituted by $BR^6_2$, $OR^6$, $SiR^6_3$, $NR^6_2$; most preferably $R^2$ is an alkylsubstituted phenyl, naphthyl, or anthracyl; most preferably $R^2$ is a 2,6 dialkylphenyl group, optionally substituted in position 4 by a group R;
$R^3$ is a divalent aliphatic or aromatic hydrocarbon group containing from 1 to 20 carbon atoms, optionally containing from 1 to 5 heteroatoms of groups 14, 15 and 16 of the periodic table of the elements and/or boron;
Preferably $R^3$ is selected from the group consisting of: $(CR^6_2)_s$ wherein s is 1 or 2,

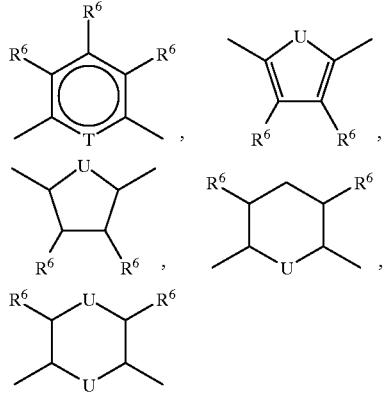

wherein
T is boron, nitrogen or phosphorus; U is boron, oxygen, nitrogen, sulphur or phosphorus;
each $R^4$, equal to or different from each other, is hydrogen or a radical which contains from 1 to 20 carbon atoms; this group optionally contains heteroatoms of group 14 to 16 of the periodic table of the elements and/or boron;
preferably $R^4$ is selected from the group consisting of: hydrogen, $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, $C_8$–$C_{20}$ alkenylaryl, optionally substituted by $BR^6_2$, $OR^6$, $SiR^6_3$ or $NR_2$;
two or more of $R^1$, $R^2$, $R^3$, $R^4$ and $R^5$ can also unite to form a from 4 to 15 membered aliphatic or aromatic ring; the ring optionally contains heteroatoms of group 14 to 16 of the periodic table of the elements and/or boron.
preferably $R^1$ is selected from the group consisting of: hydrogen, $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylakenyl, $C_8$–$C_{20}$ alkenylaryl, linear or branched, optionally substituted by $BR^6_2$, $OR^6$, $SiR^6_3$, $NR^6_2$; or $R^5OSi(R)_3$;
examples of group $CR^6_2(R^7)_aCR^6_2OSi(R)_3$ are:
—$CH_2$—$CH_2$—$OSiMe_3$; —$CH2$—$(CH_2)_p$—$CH_2$—$OSiMe_3$ wherein p ranges from 1 to 10;
—$CH_2$—O—$CH_2$—$OSiMe_3$; —$CH_2$—$C_6H_4$—$CH_2$—$OSiMe_3$; —CH(Et)—$CH_2$—$OSi(Et)_2Me$;
—$CH_2$—$CH_2$—O—$CH_2OSi(iPr)_3$; —$CH_2$—$Si(CH_3)_2$—$CH_2$—$CH_2OSi(iPr)_3$;
—$CH_2$—$CH_2$—$Si(CH_3)_2$—$CH_2OSi(iPr)_3$; —$CH_2$—$CH_2$—$CH_2$—N($CH_3$)—$CH_2$—$CH_2$—$CH_2$—$OSi(iPr)_3$;
—$C(Me)_2$—$CH_2$—$C_6H_4$—$CH_2$—$CH_2$—$OSi(C_5H_{11})_3$; —$CH_2$—$CH_2$—$C_6H_4$—O—$CH_2$—$CH_2$—$OSi(CH_2PH)_3$;
—$C(CH_3)_2$—$C(CH_3)_2$—$OSi(C_6H_4Me)_3$; —CH(Me)—CH(Me)—$OSi(Et)(Me)_2$.

In a particular embodiment the ligand of the present invention can be used for obtaining a solid catalyst component for polymerizing olefins. This solid catalyst component is obtainable by a process comprising the following steps:

a) reacting a diimino ligand of general formula I or II with a porous inorganic support;

b) treating the reaction mixture with a compound of general formula $L_qMX_2$, wherein M is selected from the group 8, 9 and 10 of the periodic table, preferably nickel, palladium, iron or cobalt; more preferably nickel; each X, equal to or different from each other, is selected from the group consisting of: halogen, hydrogen, OR, $N(R)_2$, $C_1$–$C_{20}$ alkyl or $C_6$–$C_{20}$ aryl; two X taken together can also be an aromatic or aliphatic divalent ligand, containing two equal or different donor atoms belonging to the group 14–16 of the periodic table of the elements, such as catecholate, 1,2-ethanediolate, 1,2-phenylenediamide, α-deprotonated-β-diketone or α-deprotonated-β-ketoester such as acetylacetonate or hexafluoroacetylacetonate; L is a labile ligand; for example L is a neutral Lewis base such as diethylether, tetrahydrofurane, dimethylaniline, aniline, triphenylphosphine, n-butylamine; 1,2 dimethoxyethanie (DME), cyclooctadiene, pyridine, 1,1,2,2-tetramethylendiamine, aromatic or aliphatic nitriles, sulphides, sulphoxides or thiols, triaryl phosphinies, arsines or stibines; and q is 0, 1 or 2.

As porous inorganic support, any type of inorganic oxides can be used, such as: silica, alumina, silica-alumina, aluminium phosphates and mixtures thereof, obtaining supported catalysts with contents in transition metals between 0.01 and 10% by weight, preferably between 0.1 and 4%. Preferably the inorganic support is silica.

The amount of the dilmino ligand which can be anchored in these conditions directly relates to the concentration of the reactive groups present in the support. For this reason a preferred support is silica calcinated at a temperature between 600° C. and 800° C., preferably in dry atmosphere.

The process for obtaining the solid catalyst component can be carried out in a temperature range from 0 to 200° C., in an inert solvent such as non-polar hydrocarbons, for example toluene. Besides, the resulting solid reaction product obtained by this process can be subjected to washing and subsequent filtration.

One advantage of the method here disclosed is that the procedure employed for the formation of the catalyst results in little or no side products that could hamper the polymerisation process. Thus no extra reactants other than the functionalized ligand and the silica are needed. Simple wash of the new modified silica in order to remove unreacted functionalized ligand renders a proper substrate for the second step, the attachment of the metal centre. This step can also be performed in a clean way by ligand interchange at the metal centre. Appropriate choice of the ligand accompanying initially to the metal centre is also desirable in order to facilitate the ligand interchange and to be easily removed by washing and/or evaporation.

The choice of diimino ligand and metal can result in an active catalyst for the polymerisation of olefins. The properties of the polyolefins so obtained can be finely tuned by a selection of the structural properties of the diimino ligand attached to the silica, the nature of the metal centre employed and the polymerisation conditions used (e.g. temperature, pressure, concentration of reactants, etc.).

The co-catalyst is a compound or mixture of compounds that upon reaction with the metal centres render ionic pairs in which the metal centres are alkylated cationic units and the anions are non-coordinating or weakly coordinating. Said co-catalyst is a compound or mixtures of compounds consisting of combinations of alkylating agents and Lewis acids (neutral or cationic) acting simultaneously or in differentiated steps. In cases in which the metal centre is already alkylated, only the Lewis acid, which promotes the formation of a non-coordinating or weakly coordinating anion, is needed. Illustrative but non-limiting examples of co-catalysts are: aluminoxanes (methylaluminoxane (MAO), modified methylaluminoxane (MMAO), isobutylaluminoxane (IBAO), etc.), combinations of alkylaluminiums (such as trimethylaluminium, triethylaluminium, tributylaluminium, etc.) and boron Lewis acids (such as trifluoroborate, trispentafluoroplhenylborane, tris[3,5-bis (trifluoromethyl)phenyl]borane, etc.), hydrogen Lewis acids (dimethylanilinium tetrakis(pentafluorophenyl)boron, $HBF_4$, etc.), silver Lewis acids (such as $AgBF_4$, $AgPF_6$, $AgSbF_6$, silver tetrakis[3,5-bis(trifluoromethyl)phenyl] borate etc.) or others (such as sodium tetrakis[3,5-bis (trifluoromethyl)phenyl]borate, etc.).

Compounds of fonnula I and II, wherein at least one $R^5$ is represented by the formula $CR^6_2(R^7)_aCR^6_2OSi(R)_3$, are preferably prepared by a process comprising the following steps:

1) reacting a compound represented by formula III or IV

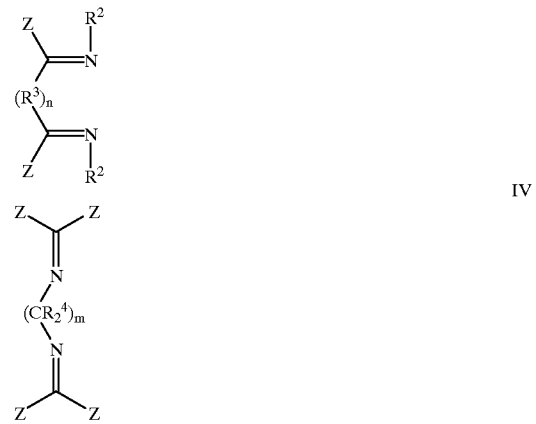

wherein each Z is independently selected from the group consisting of: $R^1$ and $CR^6_2H$, provided that at least one Z is represented by the formula $CR^6_2H$, with a Bronsted base preferably selected from the group consisting of: organolithium compounds, orgaiiosodium compounds, organopotassium compounds, organomagnesiums, sodium hydride, potassium hydride, lithium, sodium, or potassium; preferably lithium alkyl, sodium alkyl, potassium alkyl; more preferably butyllithium; and 2) contacting the obtained metallated compound with one equivalent of a compound of general formula $Y(R^7)_aCR^6_2OSi(R)_3$ wherein Y is a leaving group, preferably halogen, sulfonate groups, more preferably iodine or bromine.

While not wishing to be bound by theory, it is believed that, in the above procedure, advantage has been taken of acidity of hydrogen atoms bonded to a carbon in the alpha position to the imino group. Thus, it is believed that following a selection of the base to be used, one acidic proton at the carbon atom at the alpha position of the imino group is removed, resulting in an anionic species which is believed to be prone to act as a nucleophile in the presence of an electrophile. Thus a new bond can be formed when these two species interact. It is commonly known that such a new bond can be formed through two general pathways: by substitution or by addition. In the first case a leaving group is detached fromlthe electrophilic centre. In the second case, a bond is broken (for instance a double bond becomes a single bond).

In order to have the alkoxysilane functional group in the final ligand thus formed, this functional group, or a suitable precursor of it, is preferably already present in the electroplhile.

According to this synthetic procedure, choosing a base is desirable in order to selectively remove a hydrogen atom from the carbon atom in alpha to the imino group and, at the same time, not promoting undesired secondary reactions (for instance addition to the imine double bond). Also a suitable leaving group Y is preferably present in the electrophile in order to facilitate the formation of the new bond.

The synthetic method of the present invention has also the advantage of providing the possibility of linking more than just one functional group as long as there are more hydrogen atoms at the carbon atom in an alpha position to any of the two imino groups in the diimino precursor. It is sufficient to adjust the amount of base to be added to the original diimine in order to remove the desired number of hydrogen atoms. The process is preferably carried out under inert atmosphere for example nitrogen or argon and with dried solvents.

Non limitative examples of compounds represented by formula $Y(R^7)_a CR^6{}_2 OSi(R)_3$ are: Cl—CH$_2$—OSiMe$_3$, Cl—CH$_2$—CH$_2$—OSiMe$_3$, Cl—(CH$_2$)$_2$—CH$_2$—OSiMe$_3$, Cl—(CH$_2$)$_3$—CH$_2$—OSiMe$_3$, Cl—(CH$_2$)$_4$—CH$_2$—OSiMe$_3$, Cl—(CH$_2$)$_5$—CH$_2$—OSiMe$_3$, Cl—(CH$_2$)$_6$—Cl$_2$—OSiMe$_3$, Cl—(CH$_2$)$_7$—CH$_2$—OSiMe$_3$, Cl—CH$_2$—C$_6$H$_4$—CH$_2$—OSiMe$_3$, Cl—(CH$_2$)$_8$—CH$_2$—OSiMe$_3$, Cl—(CH$_2$)$_9$—CH$_2$—OSiMe$_3$, Cl—(CH$_2$)$_{10}$—CH$_2$—OSiMe$_3$, Cl—CH$_2$—CMe$_2$—CH$_2$—OSiMe$_3$, Cl—CH$_2$—CMe$_2$—CH$_2$—OSiMe$_3$, Cl—CH$_2$—CMe$_2$—CMe$_2$—CH$_2$—OSiMe$_3$, Cl—CH$_2$—C$_6$H$_4$—O—CH$_2$—OSiMe$_3$, Cl—CMe$_2$—CH$_2$—OSiMe$_3$, Cl—CH$_2$—CEtMe—CH$_2$—OSiMe$_3$, Cl—CH$_2$—CEt$_2$—CH$_2$—CH$_2$—OSiMe$_3$, Cl—CH$_2$—CMe$_2$—CEt$_2$—CH$_2$—OSiMe$_3$, Cl—CH$_2$—C$_6$H$_4$—O—CH$_2$—OSiMe$_3$, Cl—CEt$_2$—CH$_2$—OSiMe$_3$, Br—CH$_2$—OSiMe$_3$, Br—CH$_2$—CH$_2$—OSiMe$_3$, Br—(CH$_2$)$_2$—CH$_2$—OSiMe$_3$, Br—(CH$_2$)$_3$—CH$_2$—OSiMe$_3$, Br—(CH$_2$)$_4$—CH$_2$—OSiMe$_3$, Br—(CH$_2$)$_5$—CH$_2$—OSiMe$_3$, Br—(CH$_2$)$_6$—CH$_2$—OSiMe$_3$, Br—(CH$_2$)$_7$—CH$_2$—OSiMe$_3$, Br—CH$_2$—C$_6$H$_4$—CH$_2$—OSiMe$_3$, Br—(CH$_2$)$_8$—CH$_2$—OSiMe$_3$, Br—(CH$_2$)$_9$—CH$_2$—OSiMe$_3$, Br—(CH$_2$)$_{10}$—CH$_2$—OSiMe$_3$, Br—CH$_2$—CMe$_2$—CH$_2$—OSiMe$_3$, Br—CH$_2$—CMe$_2$—CH$_2$—OSiMe$_3$, Br—CH$_2$—CMe$_2$—CMe$_2$—CH$_2$—OSiMe$_3$, Br—CH$_2$—C$_6$H$_4$—O—CH$_2$—OSiMe$_3$, Br—CMe$_2$—CH$_2$—OSiMe$_3$, Br—CH$_2$—CEtMe—CH$_2$—OSiMe$_3$, Br—CH$_2$—CEt$_2$—CH$_2$—CH$_2$—OSiMe$_3$, Br—CH$_2$—CMe$_2$—CEt$_2$—CH$_2$—OSiMe$_3$, Br—CH$_2$—C$_6$H$_4$—O—CH$_2$—OSiMe$_3$, Br—CEt$_2$—CH$_2$—OSMie$_3$, I—CH$_2$—OSiMe$_3$, I—CH$_2$—CH$_2$—OSiMe$_3$, I—(CH$_2$)$_2$—CH$_2$—OSiMe$_3$, I—(CH$_2$)$_3$—CH$_2$—OSiMe$_3$, I—(CH$_2$)$_4$—CH$_2$—OSiMe$_3$, I—(CH$_2$)$_5$—CH$_2$—OSiMe$_3$, I—(CH$_2$)$_6$—CH$_2$—OSiMe$_3$, I—(CH$_2$)$_7$—CH$_2$—OSiMe$_3$, I—CH$_2$—C$_6$H$_4$—CH$_2$—OSiMe$_3$, I—(CH$_2$)$_8$—CH$_2$—OSiMe$_3$, I—(CH$_2$)$_9$—CH$_2$—OSiMe$_3$, I—(CH$_2$)$_{10}$—CH$_2$—OSiMe$_3$, I—CH$_2$—CMe$_2$—CH$_2$OSiMe$_3$, I—CH$_2$—CMe$_2$—CH$_2$—CH$_2$—OSiMe$_3$, I—CH$_2$—CMe$_2$—CMe$_2$—CH$_2$—OSiMe$_3$, I—CH$_2$—C$_6$H$_4$—O—CH$_2$—OSiMe$_3$, I—CMe$_2$—CH$_2$—OSiMe$_3$, I—CH$_2$—CEtMe—CH$_2$—OSiMe$_3$, I—CH$_2$—CEt$_2$—CH$_2$—CH$_2$—OSiMe$_3$, I—CH$_2$—CMe$_2$—CEt$_2$—CH$_2$—OSiMe$_3$, I—CH$_2$—C$_6$H$_4$—O—CH$_2$—OSiMe$_3$, I—CEt$_2$—CH$_2$—OSiMe$_3$, I—CH$_2$—OSiEt$_3$, I—CH$_2$—CH$_2$—OSiEt$_3$, I—(CH$_2$)$_2$—CH$_2$—OSiEt$_3$, I—(CH$_2$)$_3$—CH$_2$—OSiEt$_3$, I—(CH$_2$)$_4$—CH$_2$—OSiEt$_3$, I—(CH$_2$)$_5$—CH$_2$—OSiEt$_3$, I—(CH$_2$)$_6$—CH$_2$—OSiEt$_3$, Br—(CH$_2$)$_7$—CH$_2$—OSiPr$_3$, Br—CH$_2$—C$_6$H$_4$—CH$_2$—OSiPr$_3$, Br—(CH$_2$)$_8$—CH$_2$—OSiPr$_3$, Br—(CH$_2$)$_9$—CH$_2$—OSiPr$_3$, Br—(CH$_2$)$_{10}$—CH$_2$—OSiPr$_3$, Br—CH$_2$—CMe$_2$—CH$_2$—OSiPr$_3$, Cl—CH$_2$—CMe$_2$—CH$_2$—CH$_2$—OSiPh3, Cl—CH$_2$—CMe$_2$—CMe$_2$—CH$_2$—OSiPh$_3$, Cl—CH$_2$—C$_6$H$_4$—O—CH$_2$—OSiPh$_3$, Cl—CMe$_2$—CH$_2$—OSiPh$_3$, Cl—CH$_2$—CEtMe—CH$_2$—OSiPh$_3$, Cl—CH$_2$—CEt$_2$—CH$_2$—CH$_2$—OSiPh$_3$, Br—CH$_2$—CMe$_2$—CEt$_2$—CH$_2$—OSiMeEt$_2$, Br—CH$_2$—C$_6$H$_4$—O—CH$_2$—OSiPhMe$_2$, Br—CEt$_2$—CH$_2$—OSiEtPr2.

More preferred diimino compounds represented by formula I are:

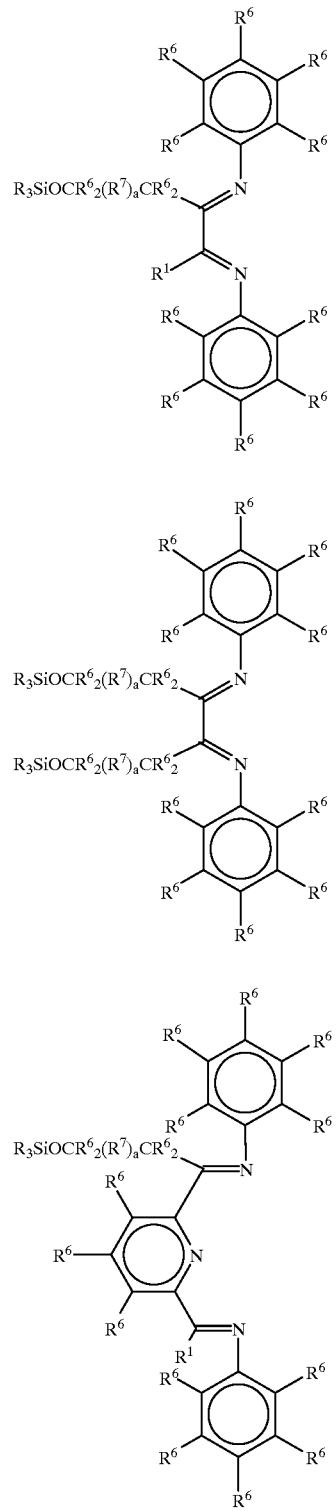

-continued
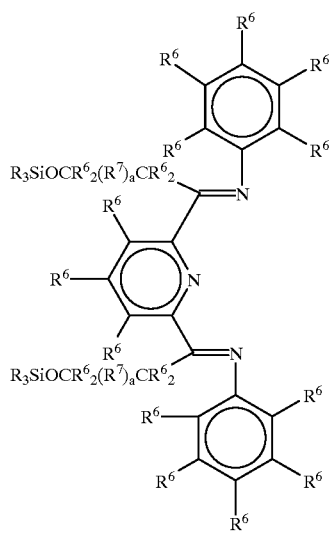
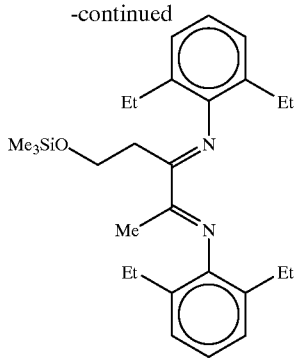
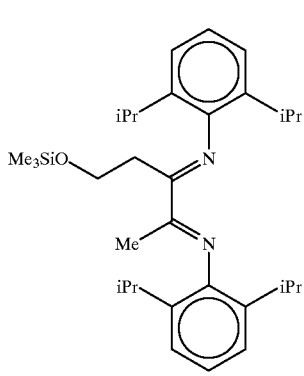
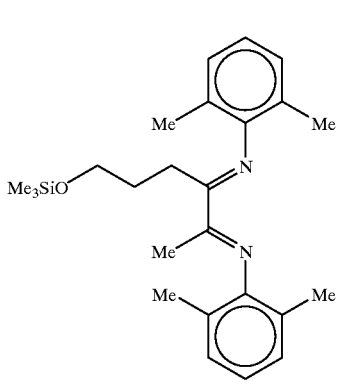
Non limiting examples of compounds according to formula I are:
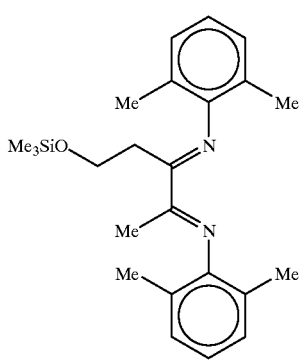
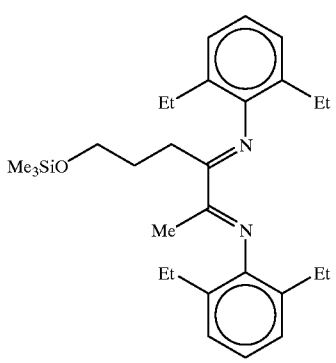

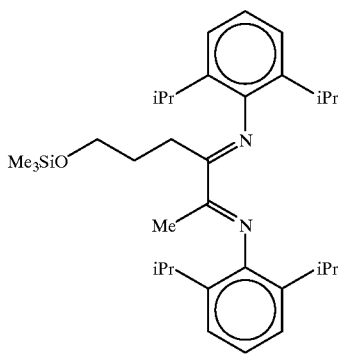
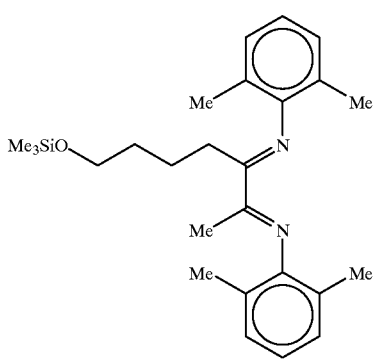
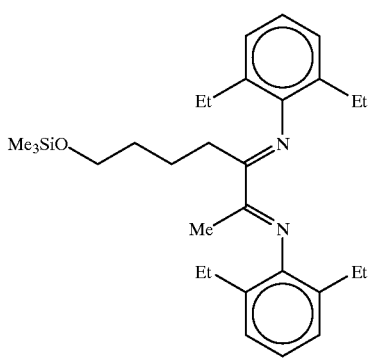
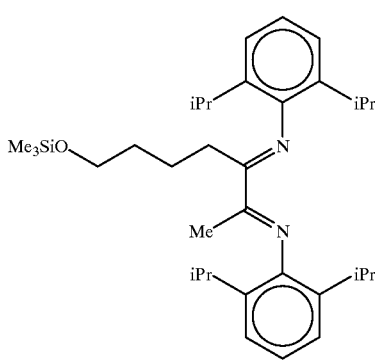
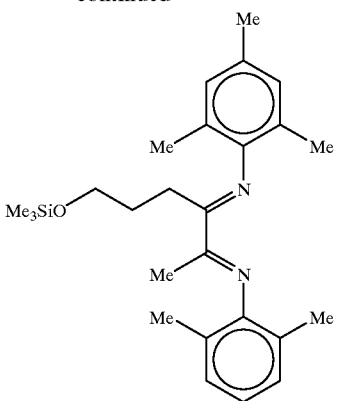
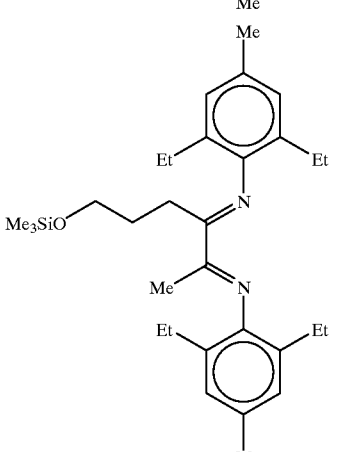
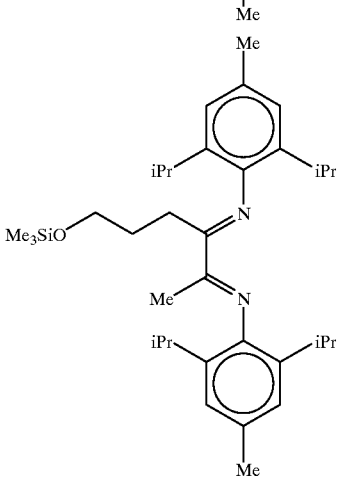
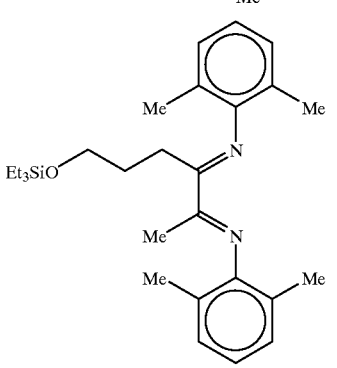

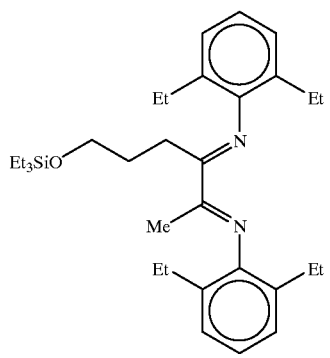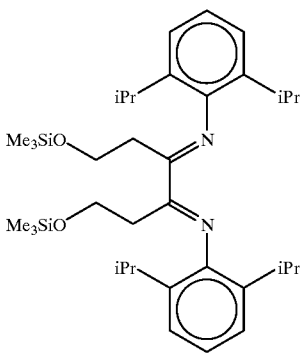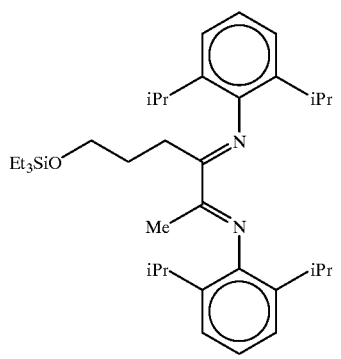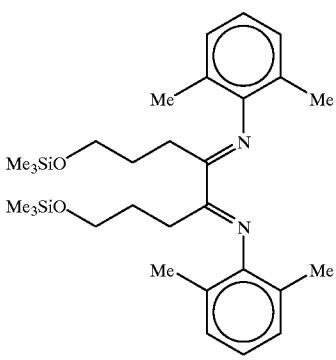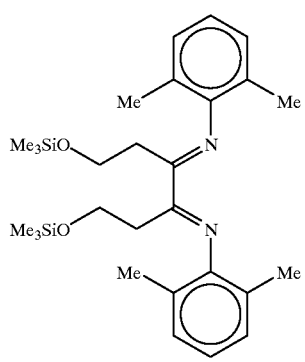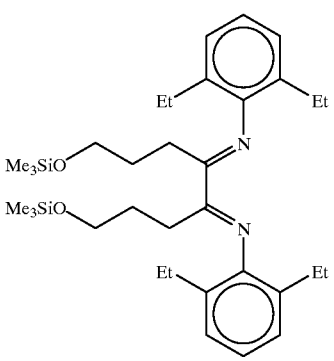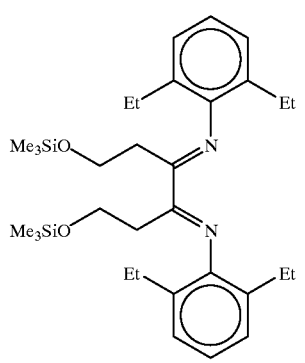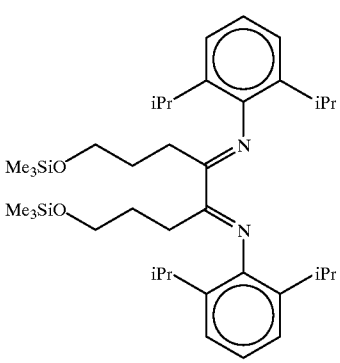

-continued
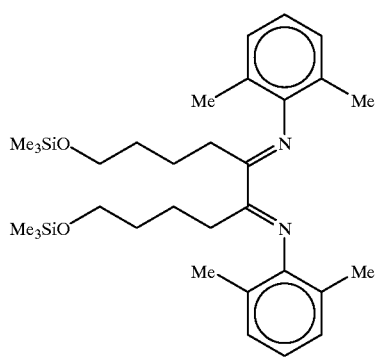
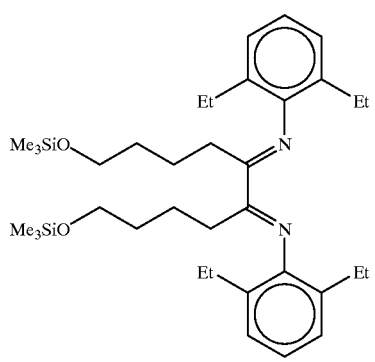
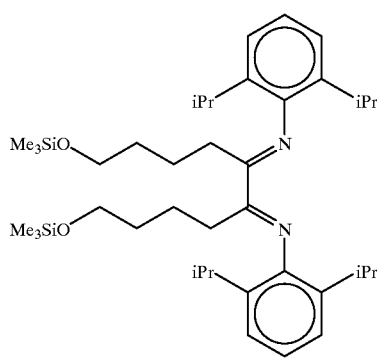
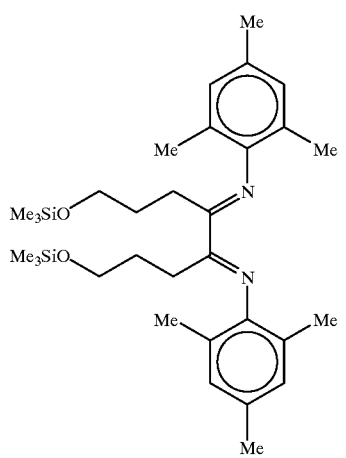
-continued
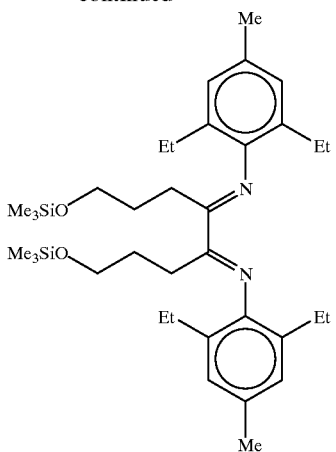
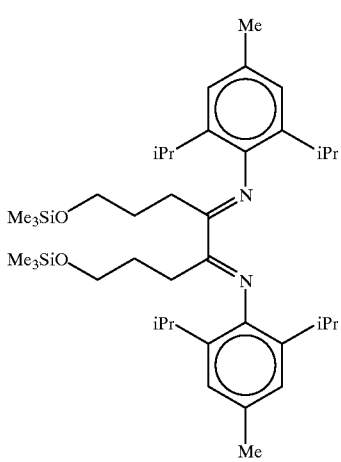
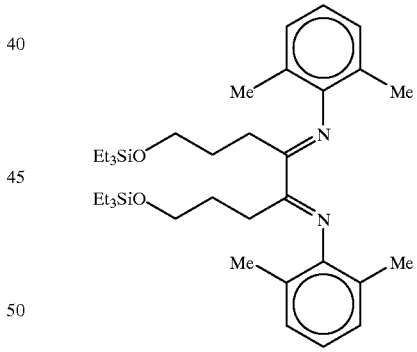
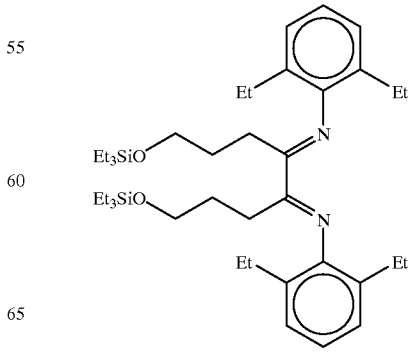

-continued
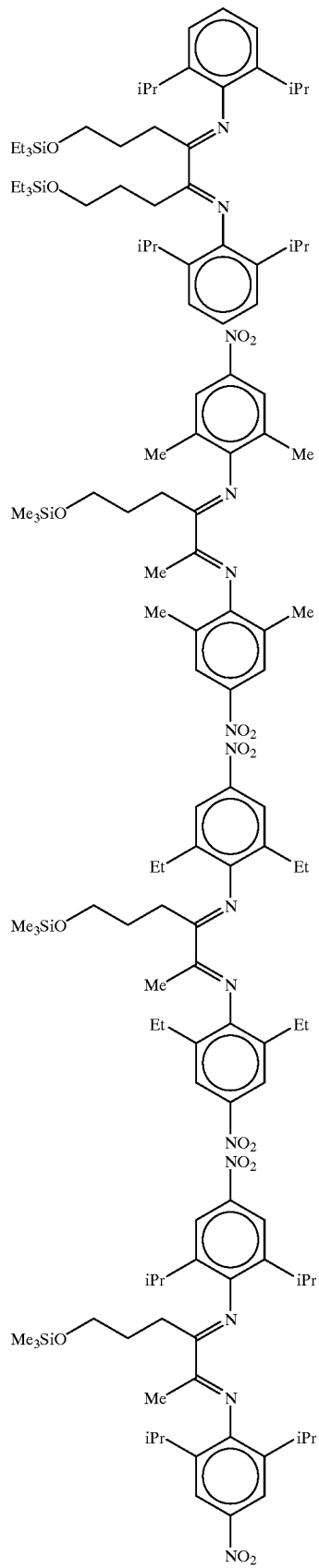
-continued
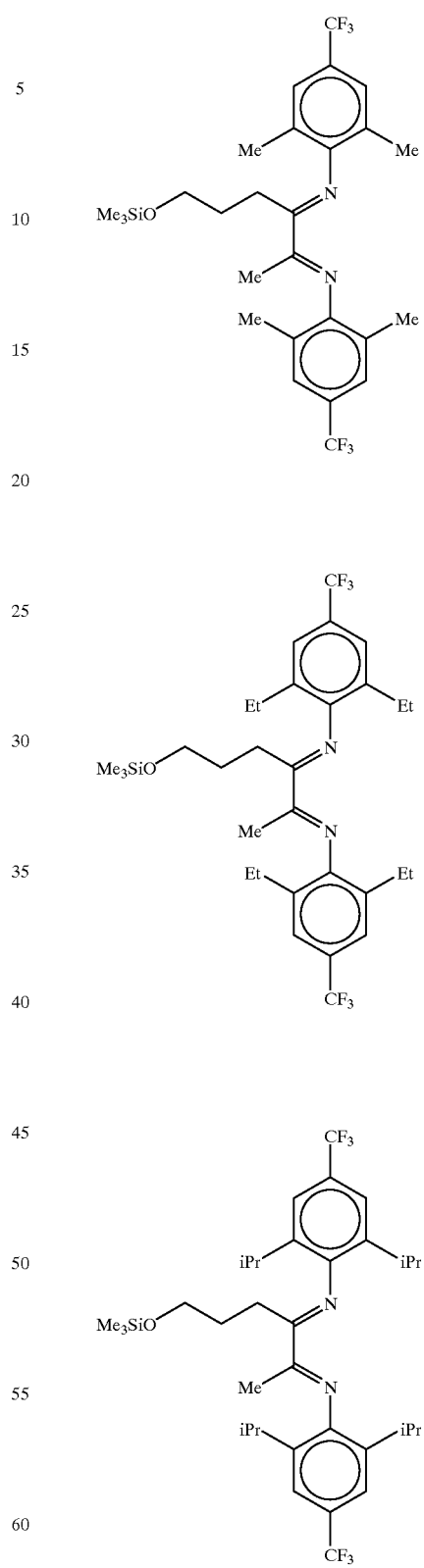

-continued
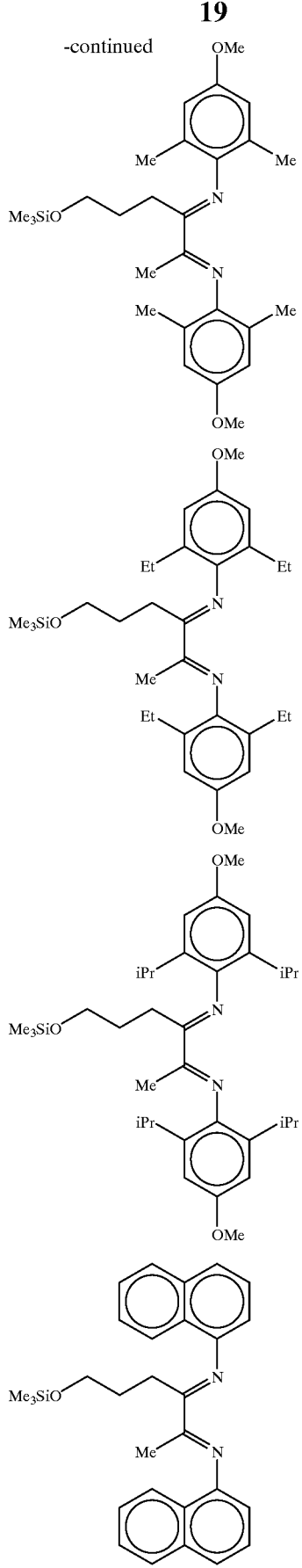
-continued
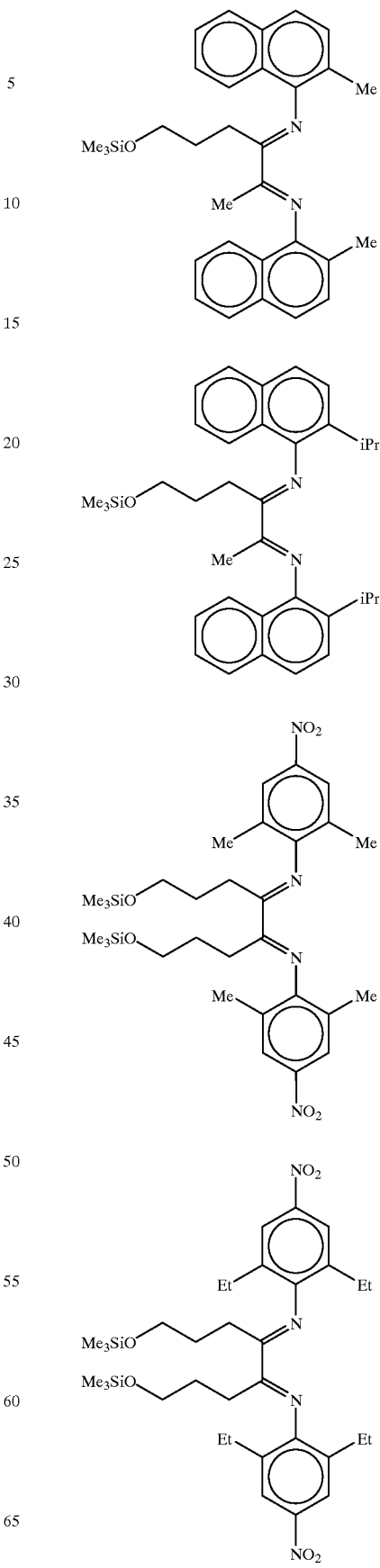

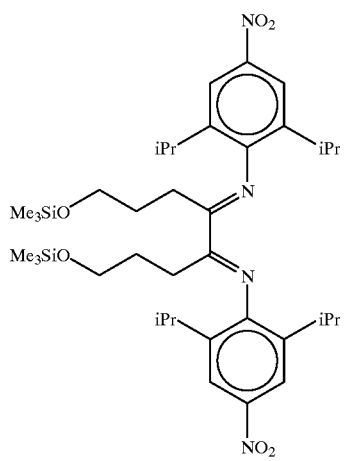
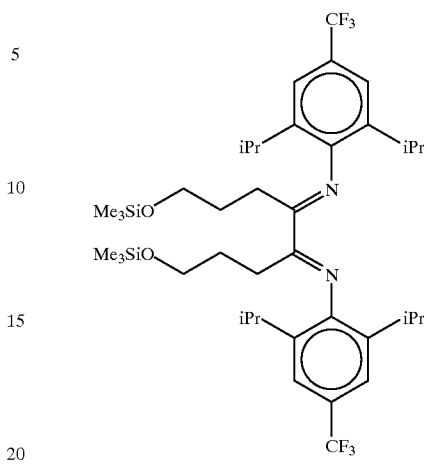
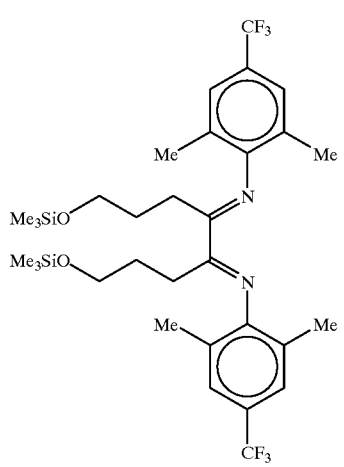
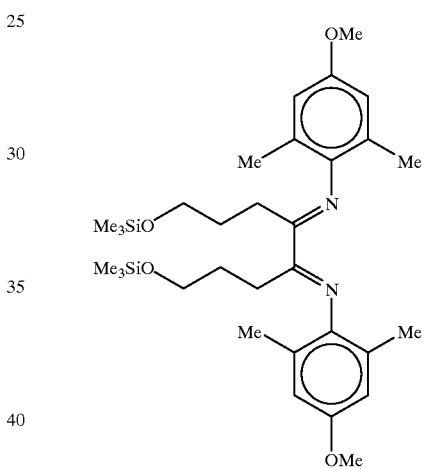
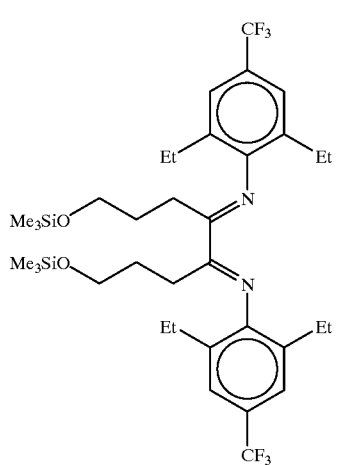
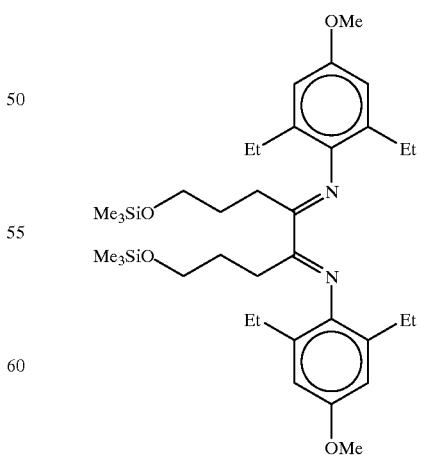

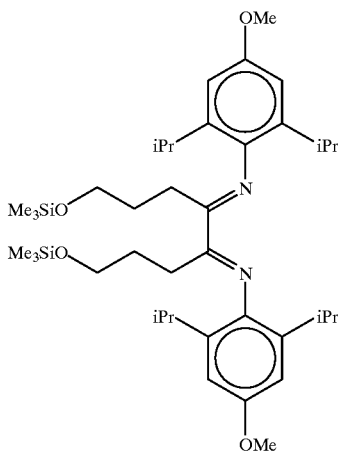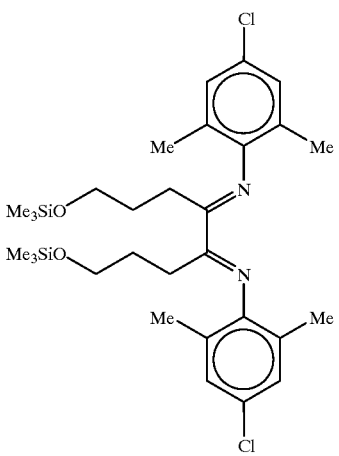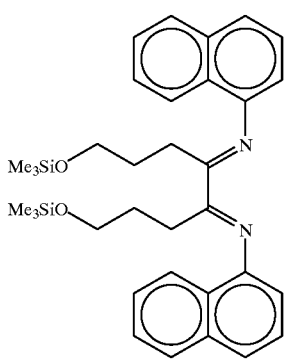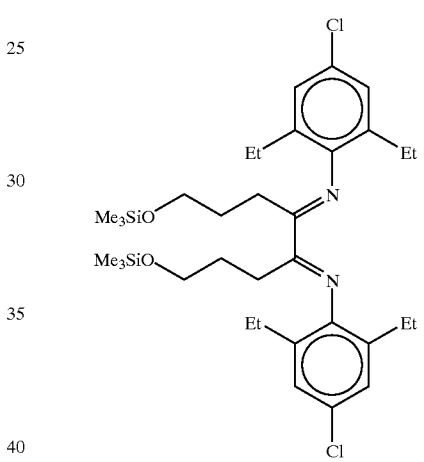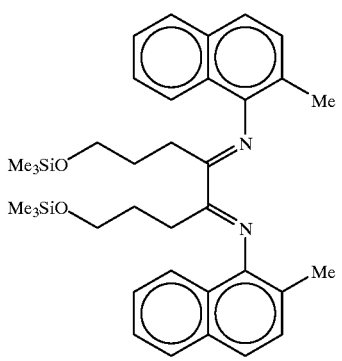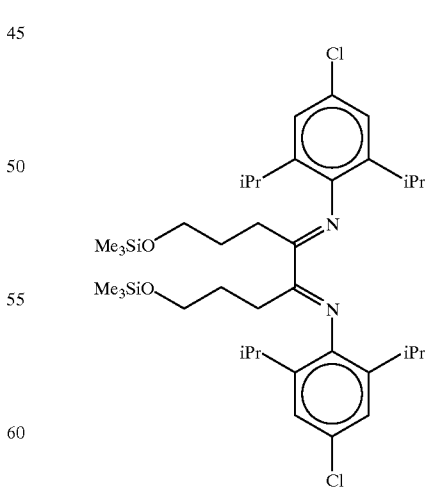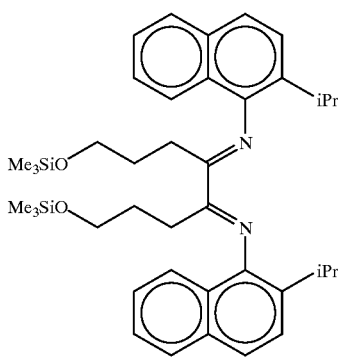

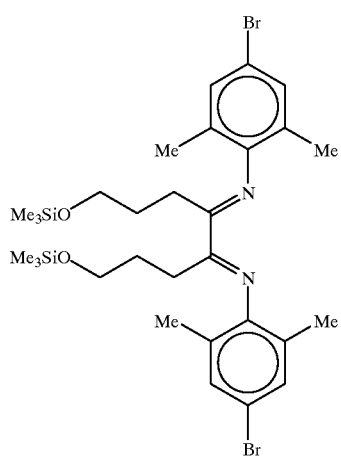
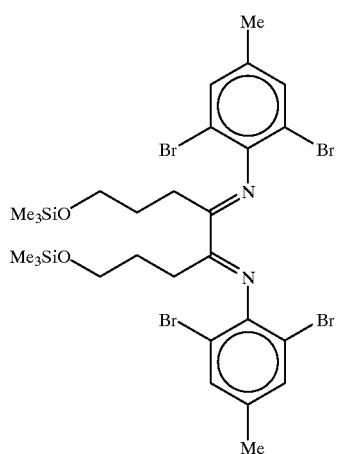
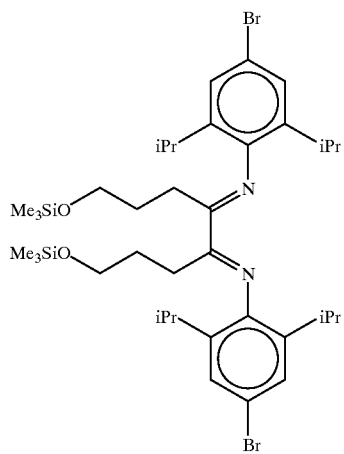
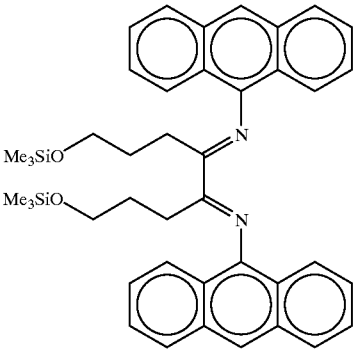
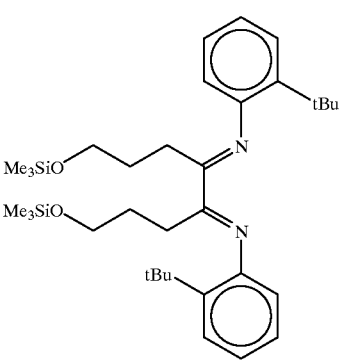
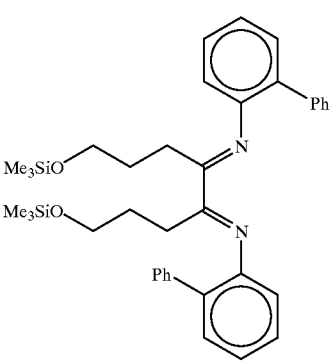
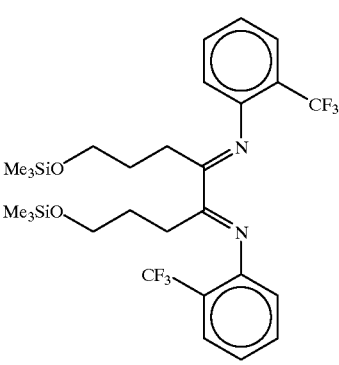

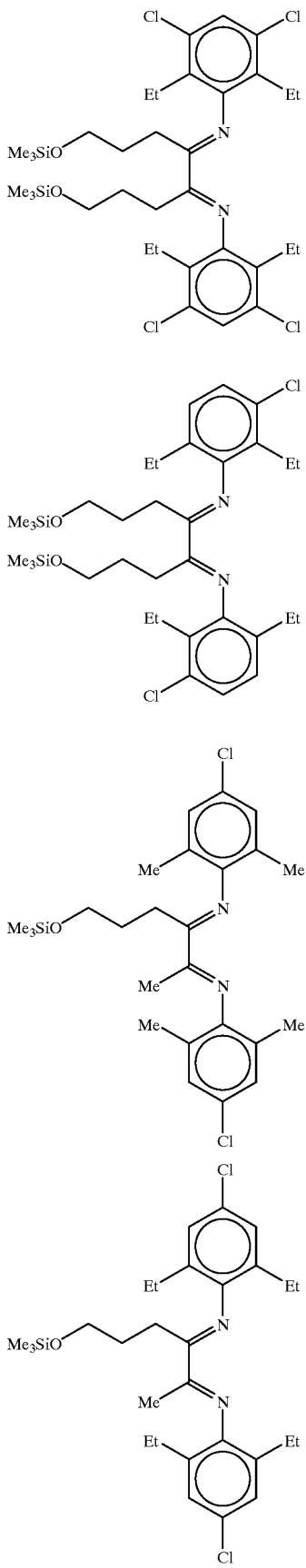
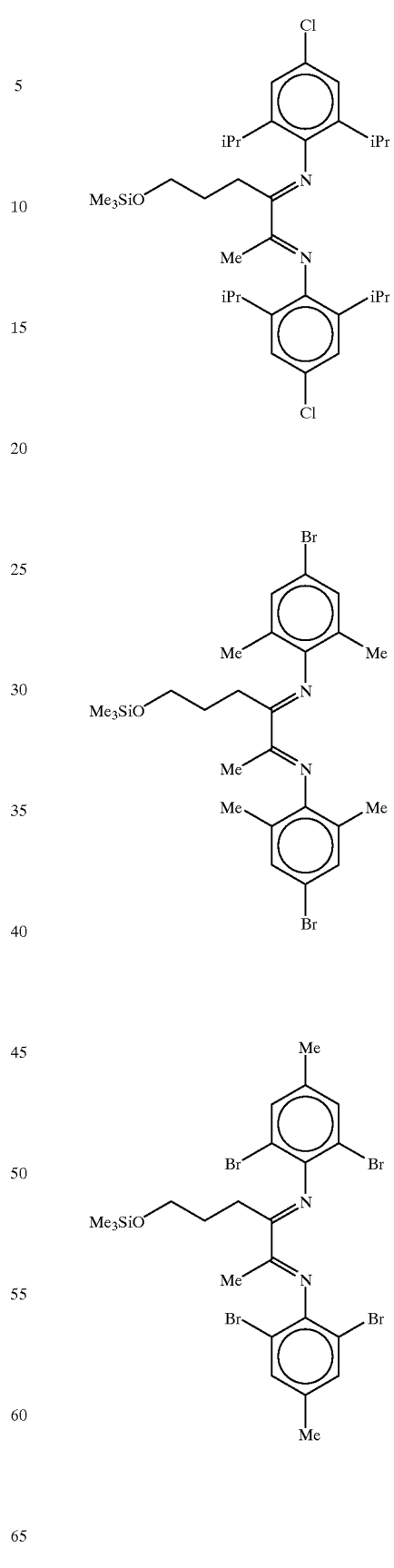

-continued
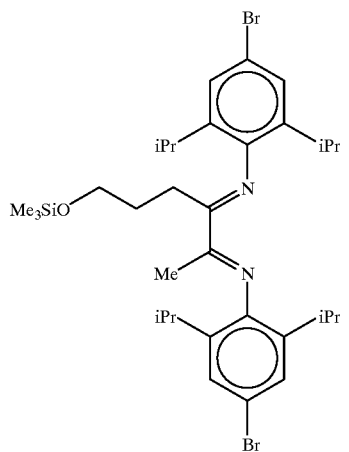
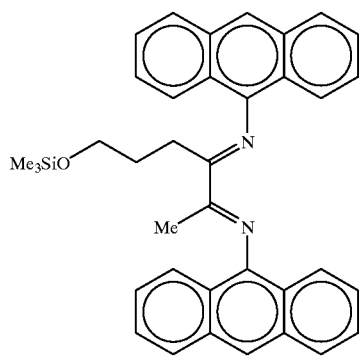
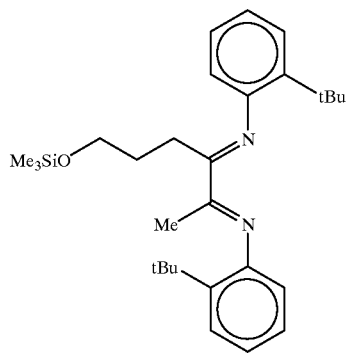
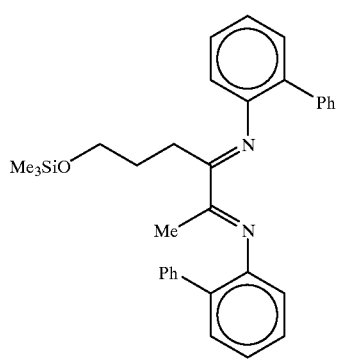
-continued
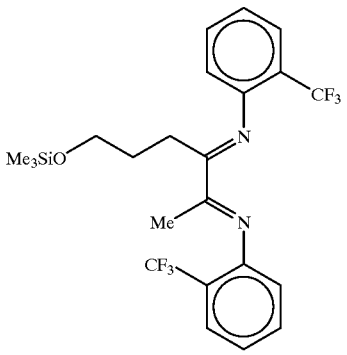
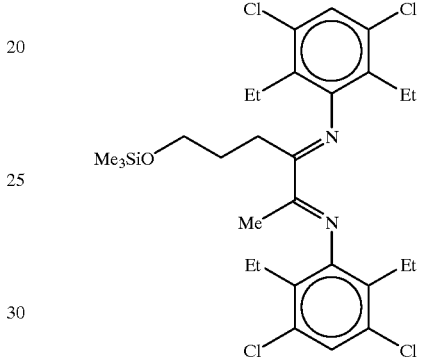
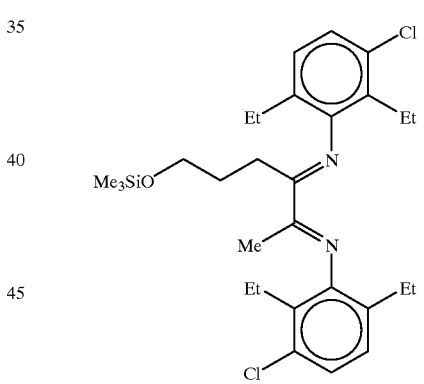
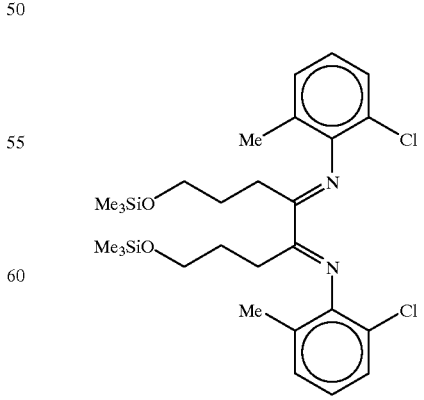

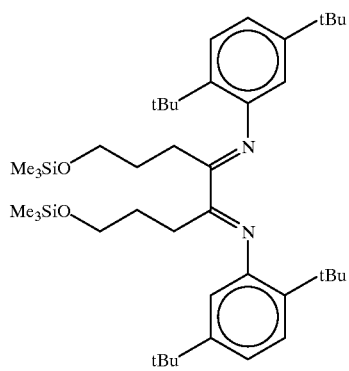
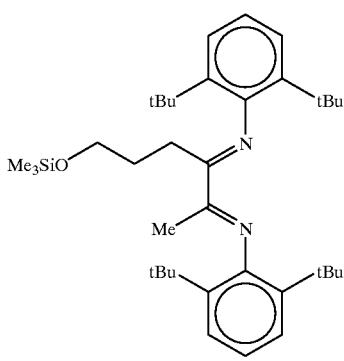
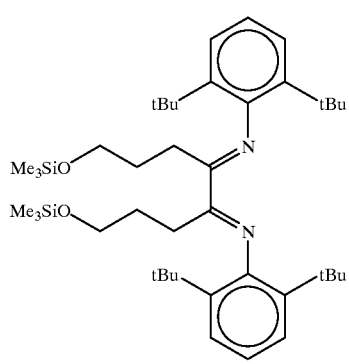
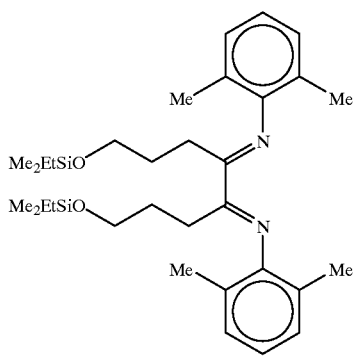
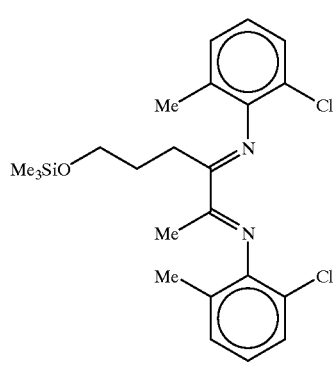
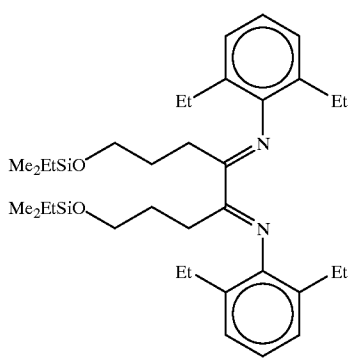
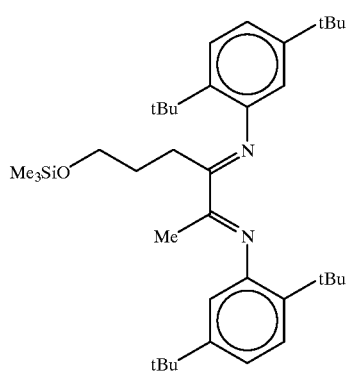
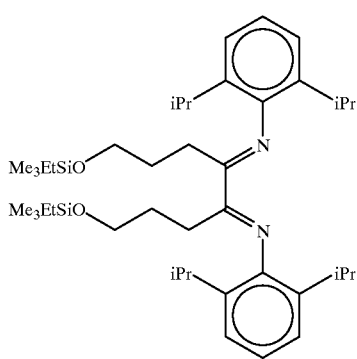

-continued
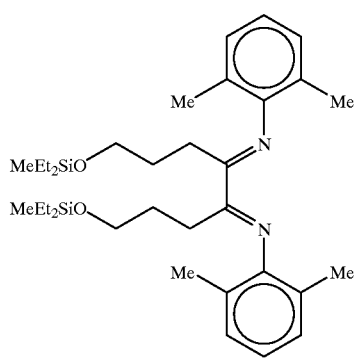
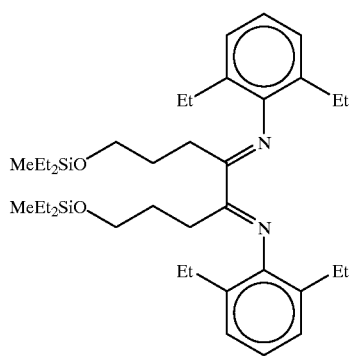
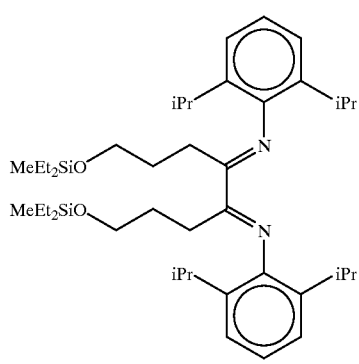
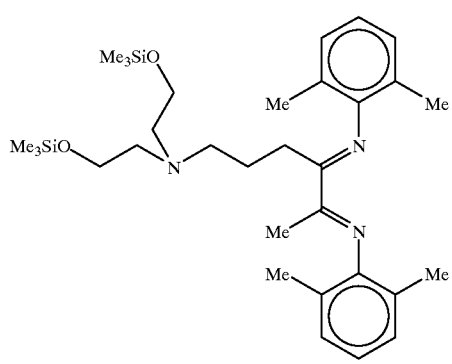
-continued
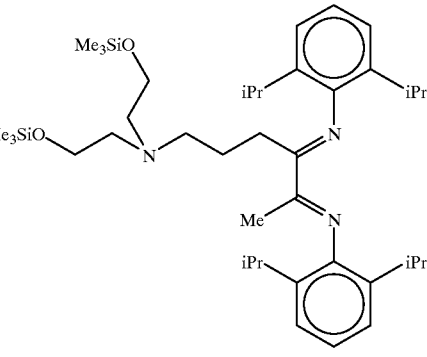
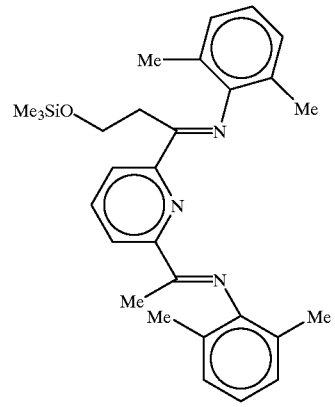
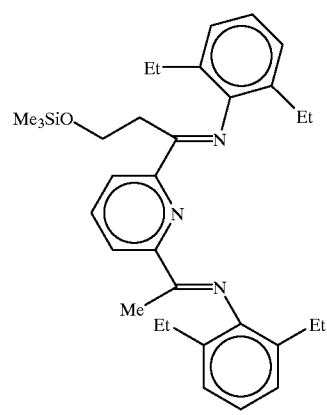
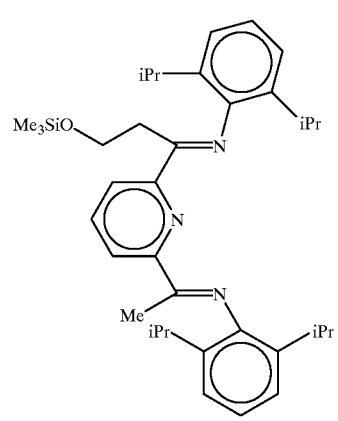

-continued
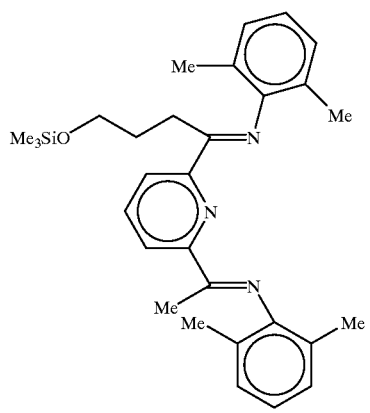
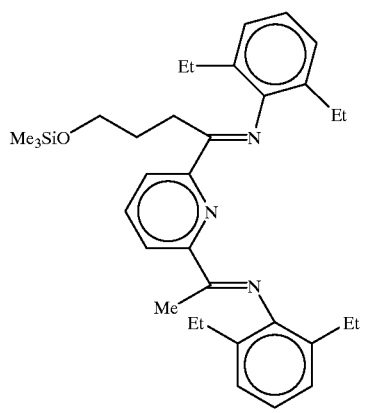
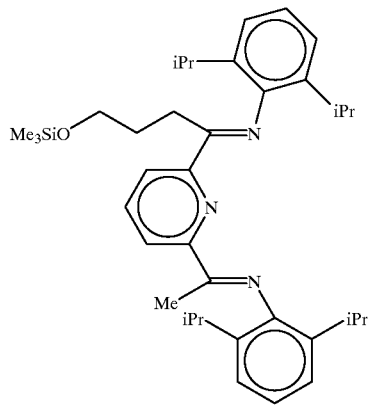
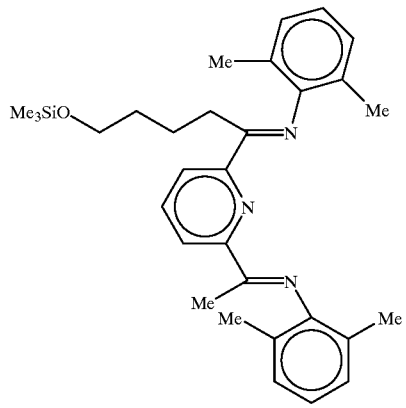
-continued
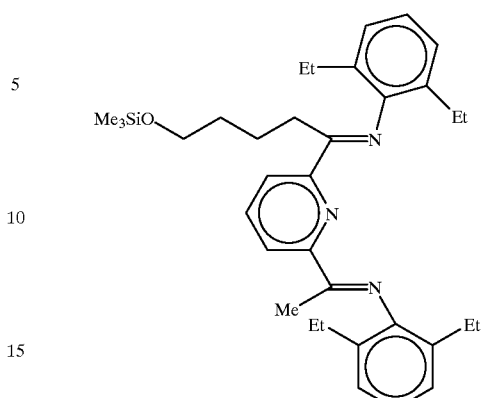
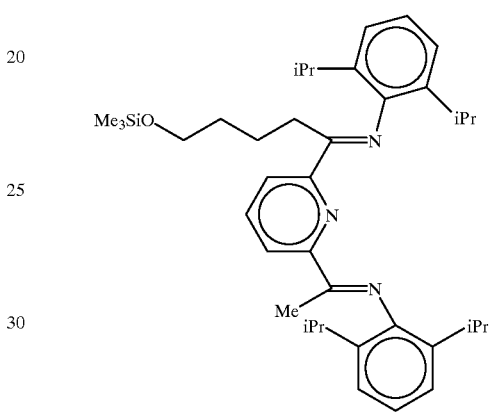
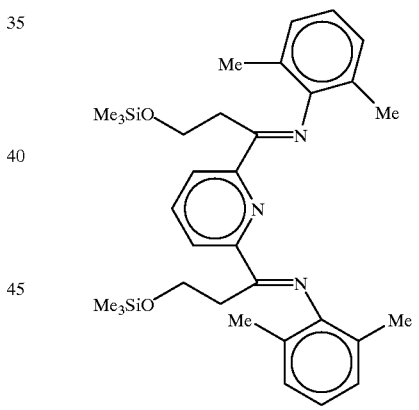
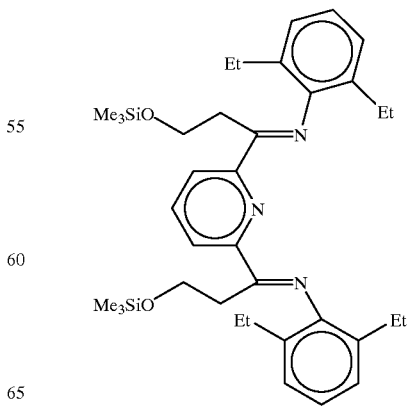

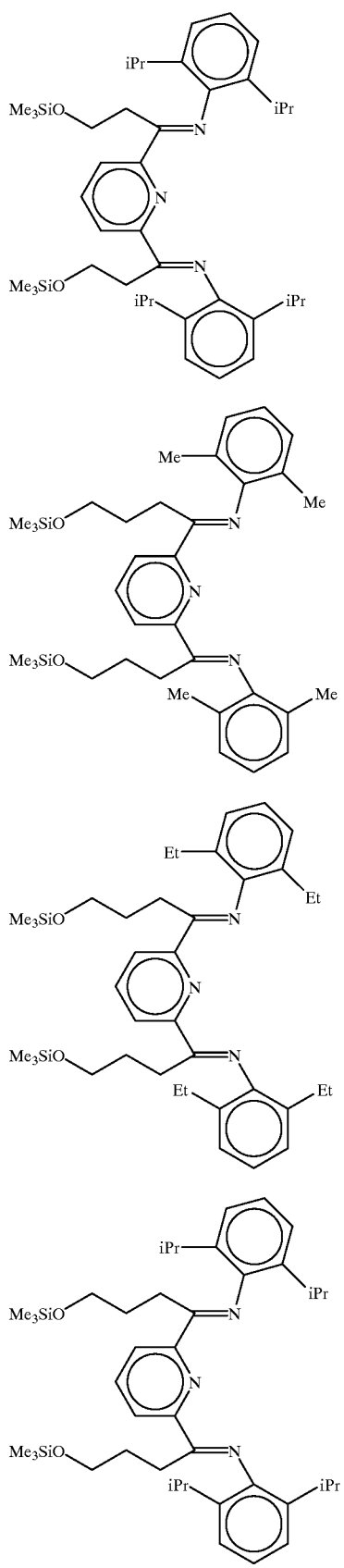
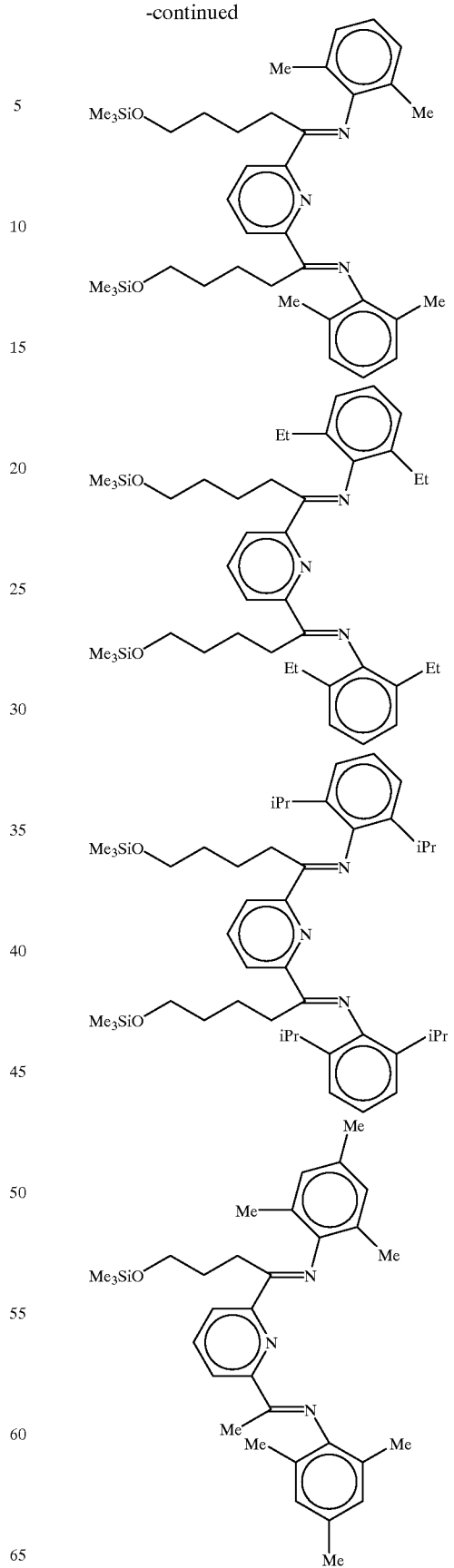

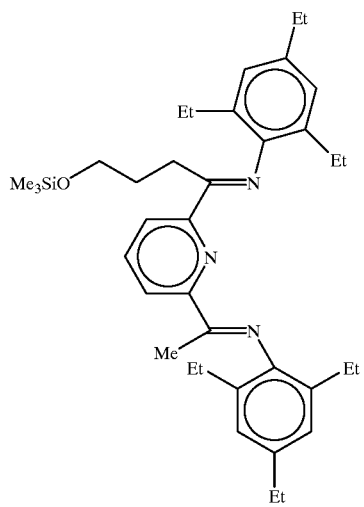
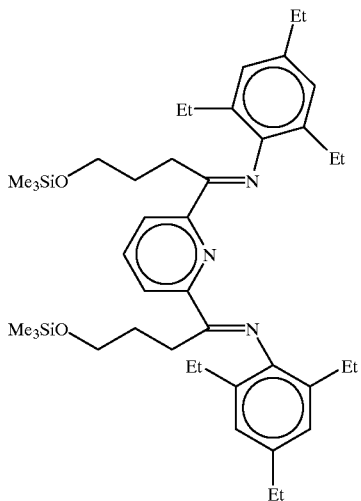
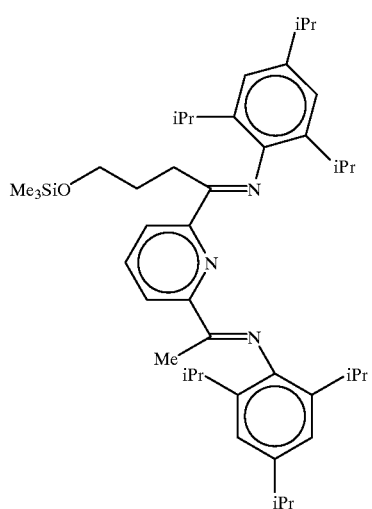
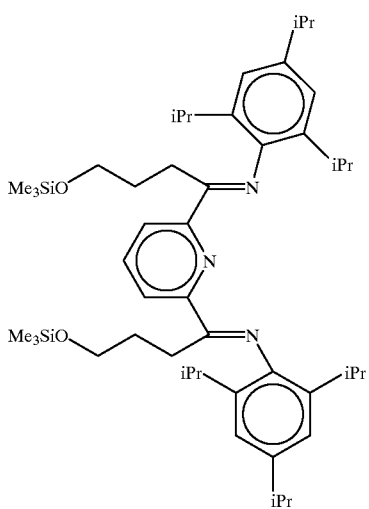
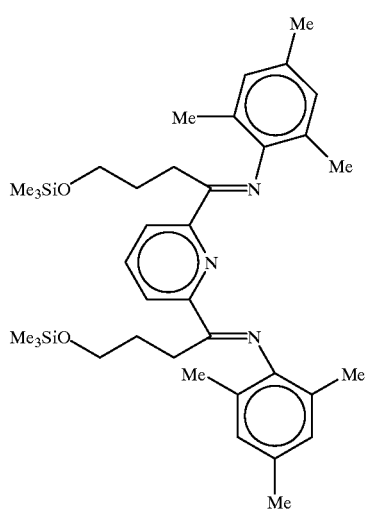
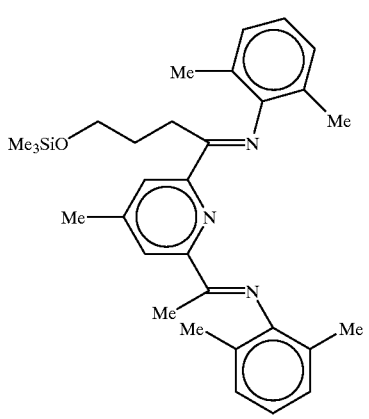

-continued
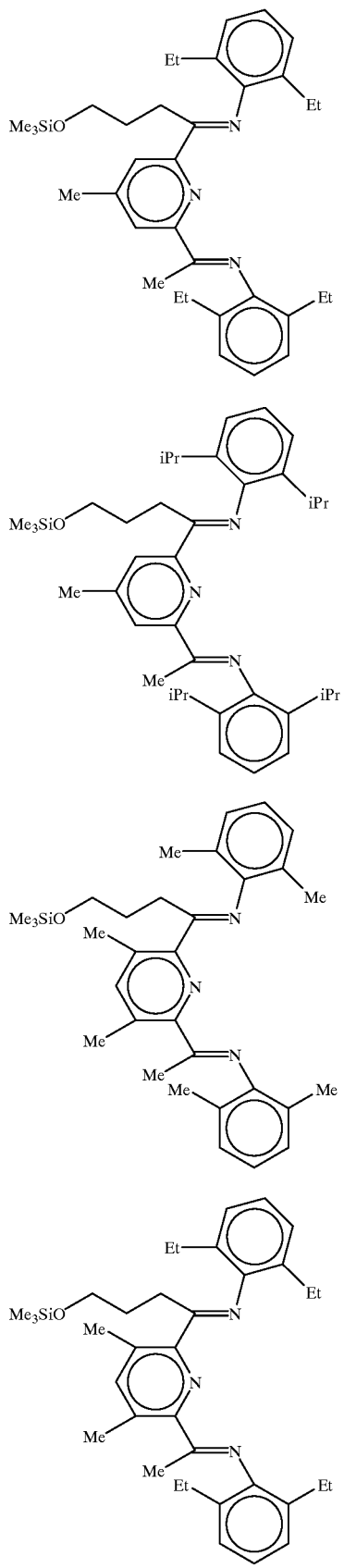
-continued
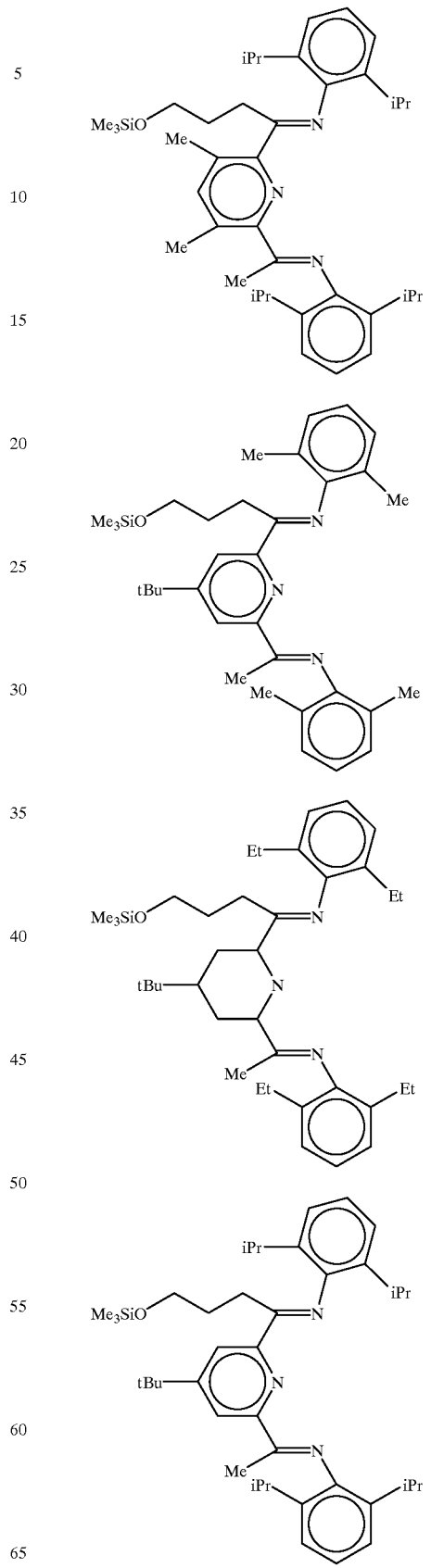

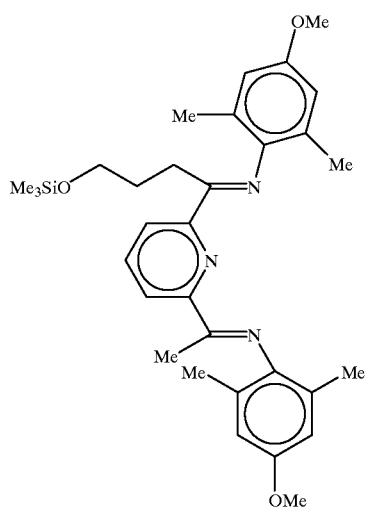
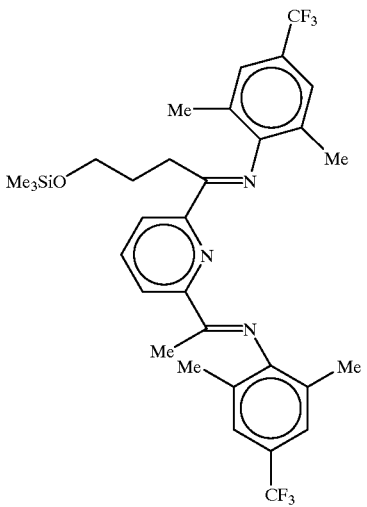
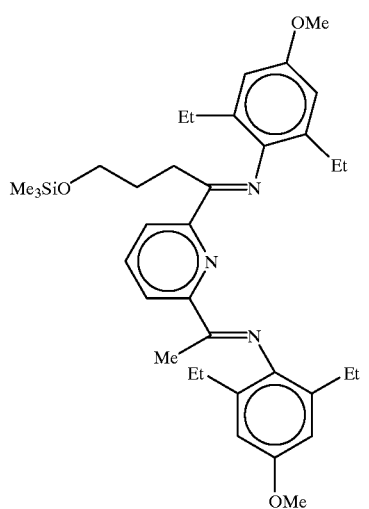
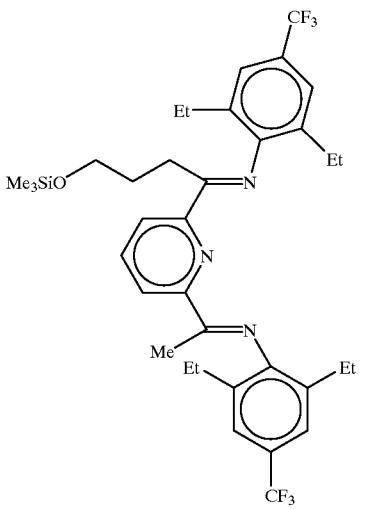
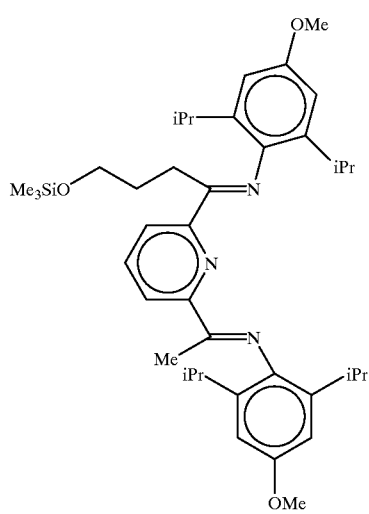
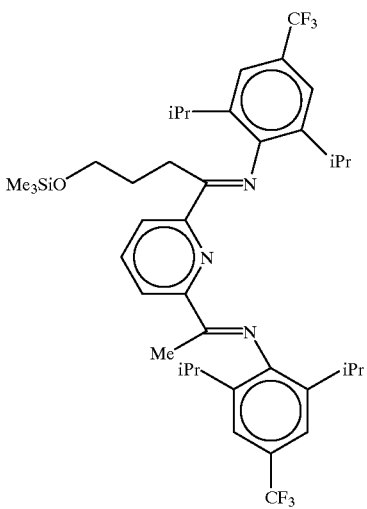

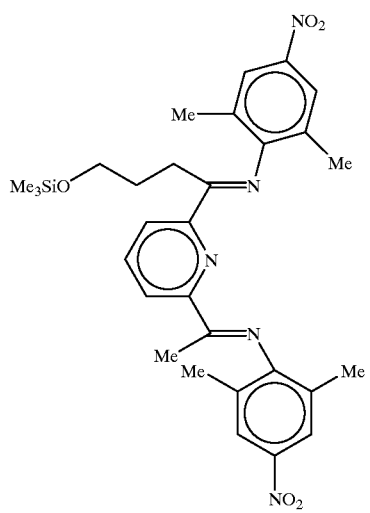
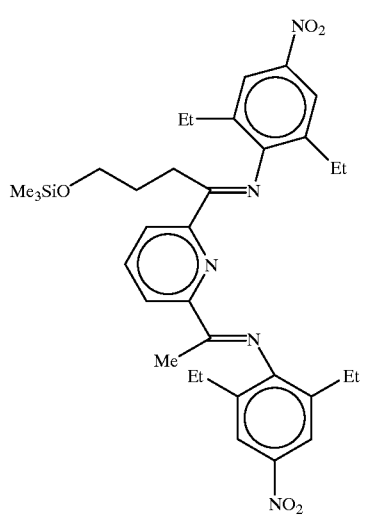
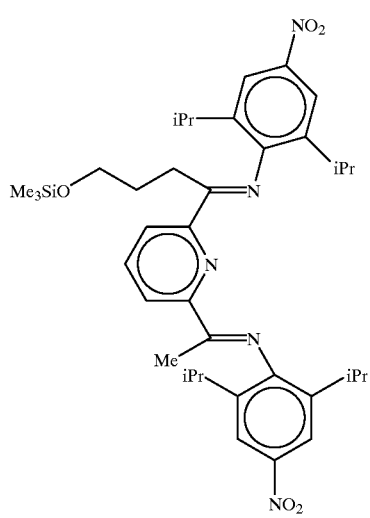
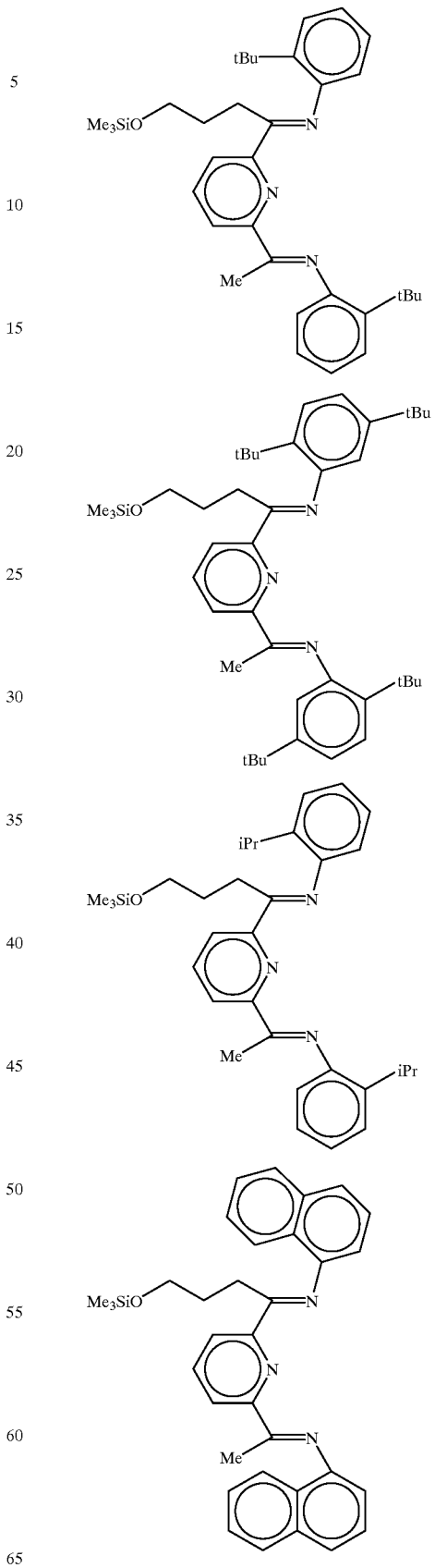

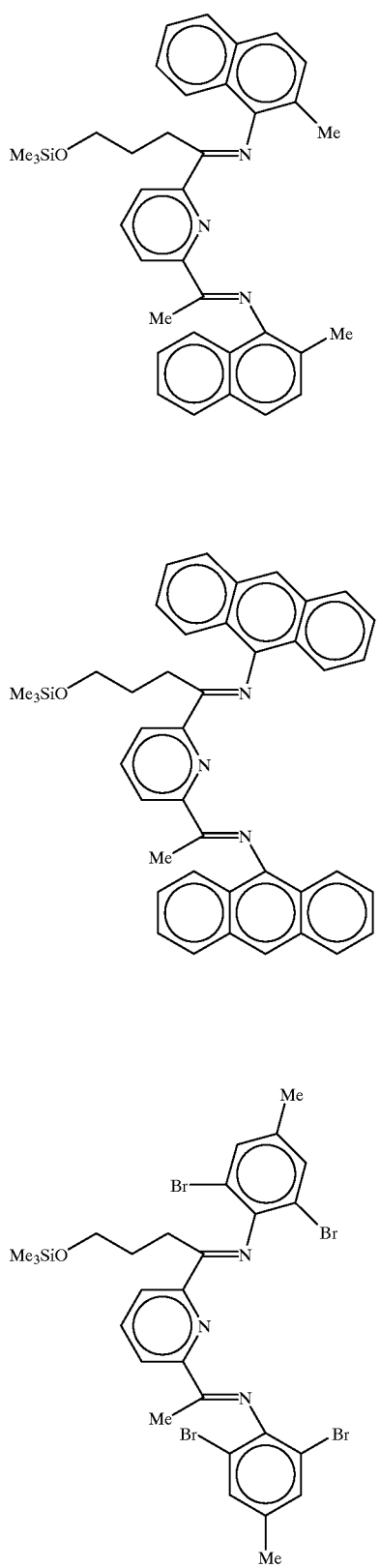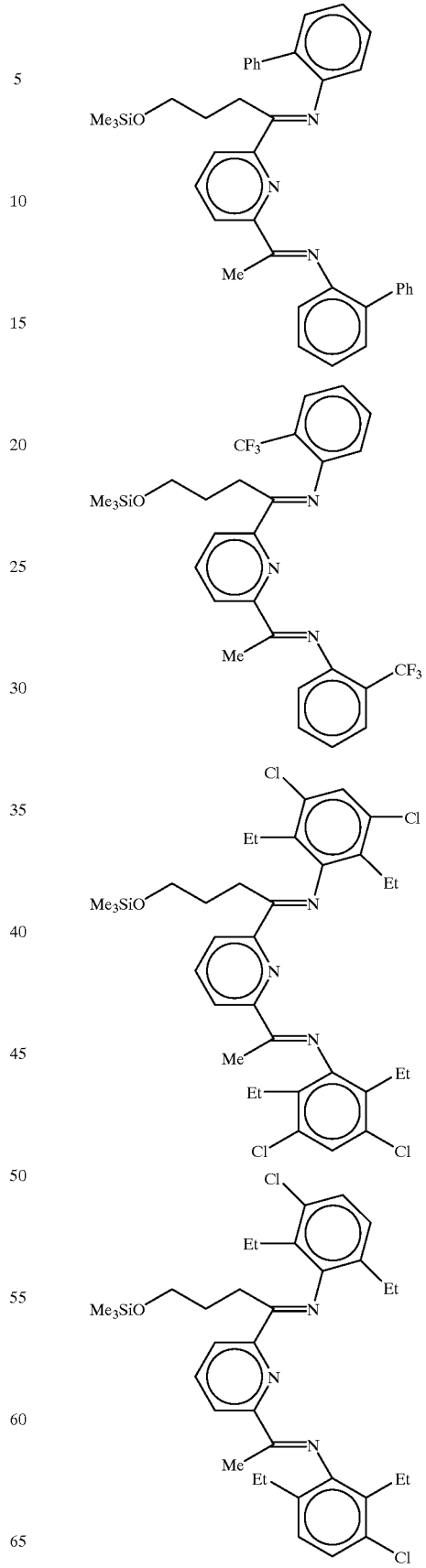

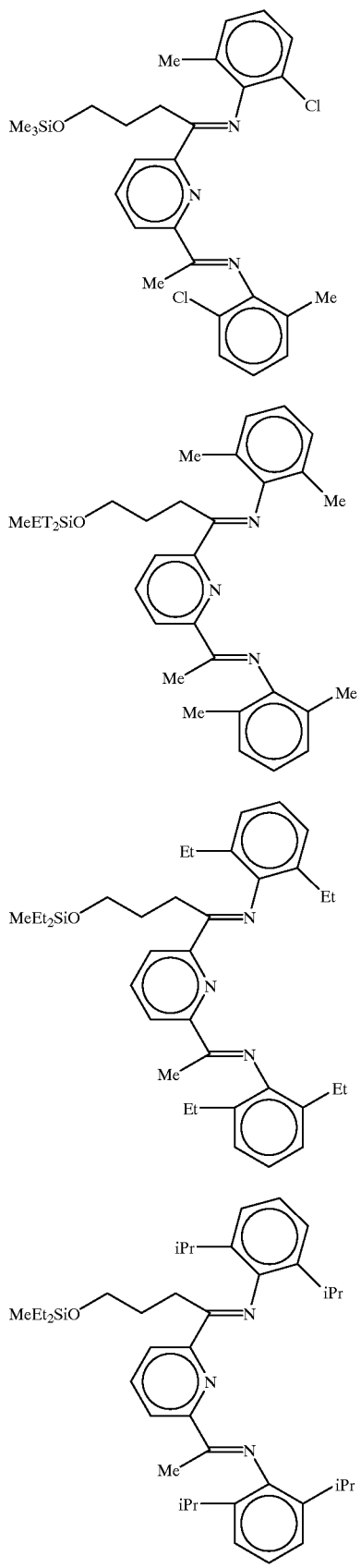

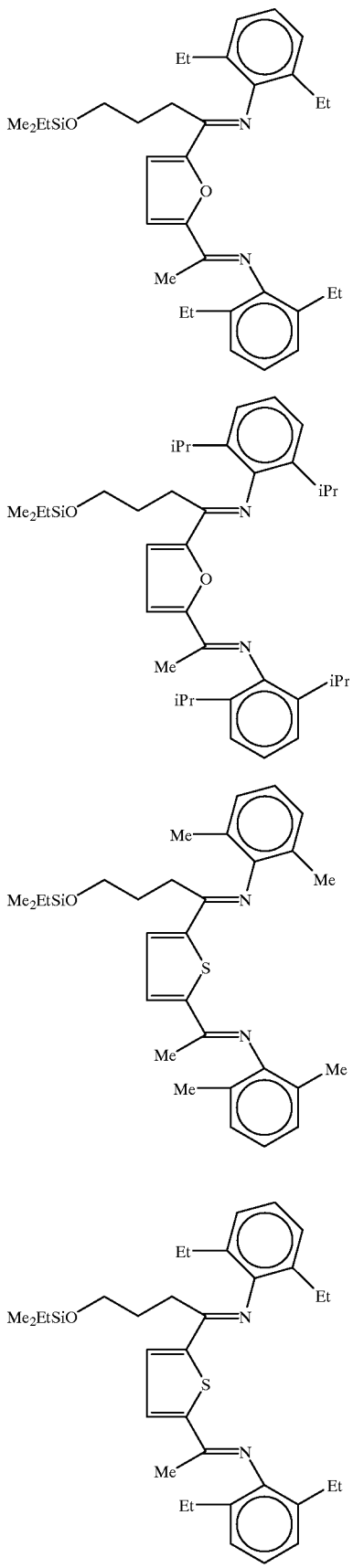

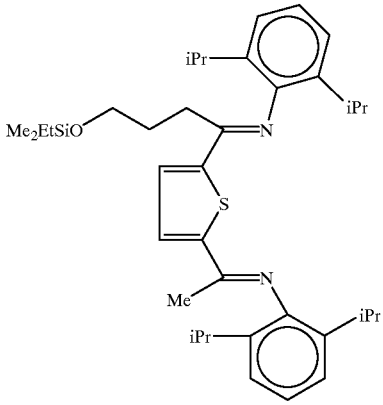

The nickel or palladium catalyst of the present invention is especially useful for the production of branched polyethylene without requiring a co-monomer.

As those of skill in the art will appreciate it, the polymerization procedure can change according to the chosen type of polymerization process (solution, suspension, slurry or gas phase).

The process comprise contacting the monomer, or, in certain cases, the monomer and the comonomer, with a catalytic composition according to the present invention.

The alpha-olefins that can be used as comonomers to obtain ethylene copolymers can be one or more $C_3$–$C_{12}$ linear or branched alpha olefin, such as propylene, butene, hexene, octene or branched ones such as the 4-methyl-1-pentene and can be used in proportions from 0.1 to 70% by weight of the total of the monomers. In the case of ethylene polymerization the density of polymers can be as low as 0.86 g/cm³.

In the particular case of the polymerization technique known as suspension process or controlled particle morphology process and in case of gas-phase process, the used temperature is preferably between 30° and 100° C., while for the solution process the usual temperature will be between 120° and 250° C.

The pressure will change according to the polymerization technique; it will range from atmospheric pressure to 350 MPa.

EXAMPLES

Preparation of functionalized diimino ligands

All operations were carried out under nitrogen or argon atmosphere following conventional Schlenk techniques. THF and diethyl ether were dried by distillation from sodium and benzophenone; $CH_2Cl_2$ was dried by distillation from calcium hydride; petroleum ether and toluene was dried by distillation from sodium. All solvents were degassed before use. The petroleum ether had a boiling point of 40–60° C.

Example 1

Preparation of 1-trimethylsilyloxy-2-iodoethane, $ICH_2CH_2OSiMe_3$.

To a solution of 2-iodoethanol (3.9ml, 50 mmol) and triethylamine (7.25, 52 mmol) in THF (40 ml) stirred at 0° C., was added trimethylsityl chloride (6.36 ml, 50 mmol). The stirring was continued for 0.5 h at the same temperature and for 6 h at room temperature. Evaporation of the solvent and distillation under vacuum affords 9.71 g of the title compound as a colourless liquid (80% yield).

$^1$H NMR (CDCl$_3$, 400 MHz) δ 3.80 (t, 2H, CH$_2$—OSiMe$_3$), 3.19 (t, 2H, CH$_2$—I), 0.14 (s, 9H, OSiMe$_3$); $^{13}$C{$^1$H} NMR (CDCl$_3$, 100 MHz) δ 63.7 (CH$_2$—OSiMe$_3$), 6.6 (CH$_2$—I), −0.3 (OSiMe$_3$).

Example 2
Monofunctionalization of diimino ligands (general procedure)

A solution of t-BuLi in pentane (1.7 M, 2.4 ml, 4.1 mmol) was added dropwise over a stirred solution of the corresponding N,N'-bis(2,6-dialkylphenyl)-1,4-diaza-2,3-dimethyl-1,3-butadiene (4 mmol) in 20 ml of THF at −80° C. After ca. 1 min, the yellow coloured solution turns to red. The reaction mixture was then stirred for 1 h and ICH$_2$CH$_2$OSiMe$_3$ (1 g, 4.1 mmol) was added. The stirring was continued for 0.5 h, and then for 6 h at the room temperature. The solvent was removed under vacuun and the residue extracted with 20 ml of petroleum ether. Filtration and evaporation of the solvent affords the product as yellowish-green oil in ca. 90% yields.

Example 2.1

Synthesis of [N,N'-bis(2,6-dimethylphenyl)-1,4-diaza-2-(3-trimethylsiloxypropyl)-3-methyl-1,3-butadiene Following the procedure of example 2, [N,N'-bis(2,6-dimethylphenyl)-1,4-diaza-2-(3-trimethylsilyloxypropyl)-3-methyl-1,3-butadiene] (L1) was obtained starting from N,N'-bis(2,6-dimetlylphenyl)-1,4-diaza-2,3-dimethyl-1,3-butadiene.

$^1$H NMR (C$_6$D$_6$, 298 K, 300 MHz): δ 7.03–6.90 (m, 6H, CH$_{Ar}$), 3.32 (t, 2H, CH$_2$—OSiMe$_3$), 2.73–2.67 (m, 2H, CH$_2$—C=NAr), 2.05 and 2.02 (s, 6H each one, o—CH$_3$), 1.99 (s, 3H, CH$_3$—C=NAr), 1.83–1.80 (m, 2H, CH$_2$—CH$_2$), −0.03 (s, 9H, OSiMe$_3$); $^{13}$C{$^1$H} NMR (C$_6$D$_6$, 298 K, 75 MHz): δ 170.9 (C=N), 167.4 (C=N), 148.8 (Cq$_{(Ar)}$), 148.4 (Cq$_{(Ar)}$), 128.0 (CH$_{Ar}$), 124.5 (Cq$_{(Ar)}$), 123.3 (CH$_{Ar}$), 62.1 (CH$_2$—OSiM$_3$), 30.1 (CH$_2$—CH$_2$—CH$_2$), 25.9 (CH$_2$—C=NAr), 17,8 (o—CH$_3$), 15.9 (CH$_3$—C=NAr), −0.8 (OSiMe$_3$). EI MS, [M]$_+$ m/z 408.

Example 2.2

Synthesis of [N,N'-bis(2,6-diisopropylphenyl)-1,4-diaza-2-(3-trimethylsiloxypropyl)-3-methyl-1,3-butadiene]

Following the procedure of example 2, [N,N'-bis(2,6-diisopropylphenyl)-1,4-diaza-2-(3-trimethylsilyloxypropyl)-3-methyl-1,3-butadiene] (L2) was obtained starting from N,N'-bis(2,6-diisopropylphenyl)-1,4-diaza-2,3-dimethyl-1,3-butadiene.

$_1$H NMR (CDCl$_3$, 400 MHz), δ 7.20–7.02 (m, 6H, CH$_{Ar}$), 3.46 (t, 3H, CH$_2$—OSiMe$_3$), 2.73 (m, 4H, CHMe$_2$), 2.55 (m, 2H, CH$_2$—C=NAr), 2.05 (s, 3H, CH$_3$C=N), 1.71 (m, 4CH$_2$—CH$_2$—CH$_2$), 1.25–1.10 (m, 24H, CH(CH$_3$)$_2$), −0.05 (s, 9H, OSiMe$_3$);

$^{13}$C{$^1$H} NMR (CDCl$_3$, 298 K. 75 MHz): δ 171.1 (C=N), 168.3 (C=N), 146.5 (Cq$_{(Ar)}$), 146.0 (Cq$_{(Ar)}$), 135.5 (Cq$_{(Ar)}$), 135.2 (Cq$_{(Ar)}$), 124.0 (CH$_{Ar}$), 123.9 (CH$_{Ar}$), 123.2 (CH$_{Ar}$), 123.1 (CH$_{Ar}$), 62.9 (CH$_2$—OSiMe$_3$), 29.6 (CH$_2$—CH$_2$—CH$_2$), 28.7 (CHMe$_2$), 26.6 (CH$_2$—C=NAr), 23.5 (CHMe$_2$), 23.0 (CHMe$_2$), 22.5 (CHme$_2$), 17.5 (CH3—C=NAr), −0.3 (OSiMe$_3$,). The parent molecular ion was observed in EI MS, [M]$^+$ 520.

Example 3
Difunctionalization of diimino ligands (general procedure)

A solution of t-BuLi in pentane (1.7 M, 2.4 ml, 4.1 mmol) was added dropwise over a stirred solution of the corresponding N,N'-bis(2,6-dialkylphenyl)-1,4-diaza-2,3-dimethyl-1,3-butadiene (2 mmol) in 20 ml of THF at −80° C. The yellow coloured solution turns bright red. The reaction mixture was then stirred for 0.5 h at −80° C., and for 0.5 h at room temperature, and then ICH$_2$CH$_2$OSiMe$_3$ (1 g, 4.1 mmol) was added. The stirring was continued for 0.5h, and for 6h at the room temperature. The solvent was removed under vacuum and the residue extracted with 20 ml of petroleum ether. Filtration and evaporation of the solvent affords the product as yellowish-green oil in ca. 90% yields.

Example 3.1
Synthesis of [N,N'-bis(2,6-dimethylphenyl)-1,4-diaza-2,3-di(3-trimethylsiloxypropyl)-1,3-butadiene]

Following the procedure of example 3, [N,N'-bis(2,6-dimethylphenyl)-1,4-diaza-2,3-di(3-trimethylsiloxypropyl)-1,3-butadienie] (L3) was obtained starting from N,N'-bis(2,6-dimethylphenyl)-1,4-diaza-2,3-dimethyl-1,3-butadiene.

$_1$H NMR (C$_6$D$_6$, 400 MHz) δ 7.02 (d, 4H, CH$_{Ar}$), 6.93 (t, 2H, CH$_{Ar}$), 3.35 (t, 4H, CH$_2$—OSiMe$_3$), 2.74 (m, 4H, CH$_2$—C=NAr), 2.10 (s, 12H, CH$_3$(ortho)), 1.86 (m, 4H, CH$_2$—CH$_2$—CH$_2$), −0.03 (s, 18H, OSiMe$_3$); $^{13}$C{$^1$H} NMR (C$_6$D$_6$, 100 MHz) δ 170.6 (C=N), 148.5 (Cq$_{(Ar)}$), 128.7 (CH$_{Ar}$), 124.5 (Cq$_{(Ar)}$), 123.2 (CH$_{Ar}$), 62.2 (CH$_2$—OSiMe$_3$), 30.1 (CH$_2$—CH$_2$—CH$_2$), 26.0 (CH$_2$—C=NAr), 18.1 (CH$_3$(ortho)), −0.9 (OSiMe$_3$). The parent molecular ion was observed in EI MS, [M]$^+$ m/z 524.

Example 3.2

Synthesis of [N,N'-bis(2,6-diethylphenyl)-1,4-diaza-2,3-di(3-trimethylsiloxypropyl)-1,3-butadiene]

Following the procedure of example 3, [N,N'-bis(2,6-diethylphenyl)-1,4-diaza-2,3-di(3-trimethylsiloxypropyl)-1,3-butadiene] (L4) was obtained starting from N,N'-bis(2,6-diethylphenyl)-1,4-diaza-2,3-dimethyl-1,3-butadiene.

$^1$H NMR (CDCl$_3$, 300 MHz): δ 7.13–7.06 (m, 6H, CH$_{Ar}$), 3.31 (t, 4H, CH$_2$—OSiMe$_3$), 2.85–2.79 (m, 4H, CH$_2$—C=NAr), 2.63–2.45 (m, 8H, CH$_2$—Me), 1.94–1.87 (m, 4H, CH$_2$—CH$_2$—CH$_2$), 1.24 (q, 12H, CH$_2$—CH$_3$), −0.04 (s, 18H, OSiMe$_3$).

Example 3.3
Synthesis of [N,N'-bis(2,6-diisopropylphenyl)-1,4-diaza-2,3-di(3-trimethylsiloxypropyl)-1,3-butadiene]

Following the procedure of example 3, [N,N'-bis(2,6-diisopropylphenyl)-1,4-diaza-2,3-di(3-trimethylsiloxypropyl)-1,3-butadiene] (L5) was obtained starting from N,N'-bis(2,6-diisopropylphenyl)-1,4-diaza-2,3-dimethyl-1,3-butadiene.

$^1$H NMR (CDCl$_3$, 400 MHz): δ 7.12 (d, 4H, CH$_{Ar}$), 7.05 (t, 2H, CH$_{Ar}$), 3.45 (t, 4H, CH$_2$—OSiMe$_3$), 2.71 (sept, 4H, CHMe$_2$), 2.53–2.47 (m, 4H, CH$_2$—C=NAr), 1.72–1.67 (m, 4H, CH$_2$—CH$_2$—CH$_2$), 1.21 (d, 12H, CHMeMe'), 1.12 (d, 12H, CHMeMe'), −0.04 (s, 18H, OSiMe$_3$); $^{13}$C NMR (CDCl$_3$, 75 MHz) δ 170.8 (C=N), 146.0 (Cq$_{(Ar)}$), 135.3 (Cq$_{(Ar)}$), 123.9 (CH$_{Ar}$), 123.1 (CH$_{Ar}$), 62.9 (CH$_2$—OSiMe$_3$), 29.4 (CH$_2$—CH$_2$—CH$_2$), 28.7 (CHMe$_2$), 26.8 (CH$_2$—C=NAr), 23.6 (CHMeMe'), 22.5 (CHMeMe'), −0.3 (OSiMe$_3$). EI MS, [M$^+$—C$_3$H$_7$] m/z 593.

Example 4
Preparation of supported catalyst precursor

Silica (XPO 2407) supplied by Grace Company was calcined according to the following procedure:

(1) Warm up from 25to 400° C. in 2 h (2) Maintain at 400° C. for 6 h (3) Warm up from 400 to 800° C. in 1 h (4) Maintain at 800° C. for 4 h (5) Cool down to room temperature under atmosphere of dry nitrogen To a given amount of the silica thus treated, an amount of ligand L3 dissolved in toluene was added. The mixture was stirred for 1 h at room temperature and then for 20 h or more at 60–70° C. Stirring of the suspension was provided at 500 rpm with a blade stirrer in order not to break-up the silica particles. Then the suspension was filtered and the solid washed 3 times with toluene. Washing can be done at 60–70° C. in order to assure complete removal of non-anchored ligand. The solid was then dried under vacuum. The approximate amount of ligand, which has been anchored onto the support, and the approximate amount of dibromo (dimethoxyethane)nickel(II) ($DME.NiBr_2$) needed in the following step are calculated from the weight of the residue obtained after removing under vacuum the solvent,. The silica was then suspended in 30 ml of dichloromethane and a small excess of $DME.NiBr_2$ dissolved in 5,0 ml of dichloromethane added. The mixture was stirred for 20 h at room temperature employing the same technique as above in order no to break-up the silica particles. The suspension was then filtered and the solid washed thoroughly with dichloromethane before being dried for 24 h under vacuum. Finally the amount of nickel in the solid was analytically determined by ICP.

Employing this general procedure the catalyst precursors of Table 1 were obtained

TABLE 1

Catalyst Precursors

| Catalyst Precursor | Ligand | g of Silica | mmol of Ligand added | mmol of Ligand recovered | mmol of $DME.NiBr_2$ added | Percentage of Ni* |
|---|---|---|---|---|---|---|
| CP1 | L3 | 4.0 | 0.78 | 0.16 | 0.48 | 0.83 |
| CP2 | L3 | 2.0 | 0.29 | 0.18 | 0.12 | 0.31 |
| CP3 | L3 | 4.0 | 0.78 | 0.43 | 0.36 | 0.38 |
| CP4 | L3 | 4.0 | 0.60 | 0.18 | 0.44 | 0.83 |

*Measured by ICP

Example 5
Polymerization, general procedures

Example 5.1
Polymerization performed at 4 bar of ethylene:
Reactor Volume: 1,3 L; Solvent: n-heptane (600 ml); Co-Catalyst: MAO 10% in toluene from Witco.

The reactor was filled with the given amount of solvent, degassed and saturated with fib ethylene at 3.75 bar at the set temperature. Then the co-catalyst was injected into the reactor. For the addition of the catalyst precursor from Table 1, the following procedure was followed: in a dry-box, a hollow stainless steel column fitted with a ball valve at each end was filled with the required weight of the solid catalyst and then filled-up with dry heptane. The column was taken outside the dry box with both valves closed and then connected vertical wise to the ethylene line (at the top end) and the reactor system (at the bottom end). The top valve was opened in order to let ethylene in at 4 bar before opening the bottom valve to allow the drop of the catalyst inside the reactor pushed by the ethylene flow. The ethylene gas consumed during polymerisation was immediately replaced by free flow from the ethylene line in order to keep a pressure of 4 bar. After the given reaction time, the polymerisation was stopped by fast degassing and depressurisation of the system and then by adding the polymerisation mixture to methanol with a few drops of HCl. The polymer was recovered by filtration, washed and dried at 10 mm Hg/70° C. for 20 h. The conditions and resulting polymer characteristics are shown in Table 2

Example 5.2
Polymerization performed at pressures higher than 4 bar of ethylene:

Reactor Volume: 1 L; Solvent: isobutane (500 ml at ca. 20 bar); Co-Catalyst: MAO 10% in toluene from Witco. A stainless steel reactor was used. The co-catalyst was injected into the reactor. Then it was filled with the isobutane and saturated with ethylene at the set temperature and pressures. For the addition of the catalyst precursor from Table 1, a similar procedure as the one employed at 4 bar was followed. After the given reaction time, the polymerisation was stopped by fast degassing and depressurisation of the system and then by adding the polymerisation mixture to methanol with a few drops of HCl. The polymer was recovered by filtration, washed and dried at 10 mm Hg/70° C. for 20 h. Conditions and resulting polymer characteristics are shown in Table 2.

TABLE 2

Polymerisation Experiments

| Essay | Catalyst Precursor | mmol Ni | Co-Catalyst | Al/Ni | P(bar)[1] | T (° C.) | t (min) | g PE | Activity[2] | Mw | MWD | Total Branches[3] | Me[3] | Hex +[3] |
|---|---|---|---|---|---|---|---|---|---|---|---|---|---|---|
| E1 | CP1 | 0.0141 | MAO | 481 | 4 | 45 | 60 | 1.88 | 3.33E+04 | 325.600 | 2.82 | 8.49 | 7.13 | 0.34 |
| E2 | CP1 | 0.0141 | MAO | 541 | 4 | 45 | 60 | 2.29 | 4.06E+04 | 421.200 | 2.42 | 17.38 | 16.28 | 0.44 |
| E3 | CP2 | 0.0204 | MAO | 152 | 4 | 45 | 120 | 10.8 | 6.62E+04 | 376.800 | 3.53 | 9.79 | 8.32 | 1.47 |
| E4 | CP2 | 0.0204 | MAO | 152 | 4 | 60 | 60 | 5.39 | 6.61E+04 | 386.500 | 8.86 | 18.20 | 18.20 | 0.00 |
| E5 | CP2 | 0.0202 | MAO | 154 | 4 | 80 | 60 | 3.81 | 4.72E+04 | 317.000 | 5.46 | 33.00 | 27.94 | 2.77 |
| E6 | CP3 | 0.0129 | MAO | 525 | 4 | 45 | 60 | 4.16 | 8.06E+04 | 279.700 | 2.84 | 8.11 | 8.11 | 0.00 |
| E7 | CP3 | 0.0129 | MAO | 525 | 4 | 45 | 120 | 6.9 | 6.69E+04 | 294.900 | 3.12 | 10.75 | 9.98 | 0.00 |
| E8 | CP3 | 0.0129 | MAO | 525 | 4 | 45 | 240 | 9.2 | 4.46E+04 | 346.900 | 2.81 | 9.16 | 9.16 | 0.00 |
| E9 | CP4 | 0.0049 | MAO | 1140 | 4 | 45 | 30 | 1 | 1.02E+05 | 321.300 | 3.1 | 14.78 | 14.78 | 0.00 |
| E10 | CP4 | 0.0141 | MAO | 997 | 4 | 45 | 30 | 2.57 | 9.11E+04 | 374.000 | 3.11 | 17.02 | 17.02 | 0.00 |
| E11 | CP4 | 0.0141 | MAO | 548 | 4 | 45 | 60 | 4.11 | 7.29E+04 | 365.300 | 3.11 | 11.18 | 11.18 | 0.00 |
| E12 | CP4 | 0.0141 | MAO | 379 | 4 | 45 | 60 | 3.51 | 6.22E+04 | 358.700 | 2.9 | 16.41 | 16.41 | 0.00 |
| E13 | CP4 | 0.0141 | MAO | 164 | 4 | 45 | 60 | 2.61 | 4.63E+04 | 332.200 | 3.09 | 12.63 | 12.63 | 0.00 |
| E14 | CP4 | 0.0141 | MAO | 1200 | 27 | 80 | 60 | 5.23 | 1.37E+04 | 343.800 | 3.88 | 9.96 | 9.22 | 0.74 |
| E15 | CP4 | 0.0141 | MAO | 200 | 27 | 80 | 60 | 4.58 | 1.20E+04 | 299.900 | 3.31 | 9.03 | 9.03 | 0.00 |
| E16 | CP4 | 0.0141 | MAO | 400 | 27 | 80 | 60 | 4.49 | 1.18E+04 | 309.900 | 3.08 | 10.22 | 10.22 | 0.00 |

TABLE 2-continued

Polymerisation Experiments

| Essay | Catalyst Precursor | mmol Ni | Co-Catalyst | Al/Ni | P(bar)[1] | T (° C.) | t (min) | g PE | Activity[2] | Mw | MWD | Total Branches[3] | Me[3] | Hex +[3] |
|---|---|---|---|---|---|---|---|---|---|---|---|---|---|---|
| E17 | CP4 | 0.0141 | MAO | 1200 | 10 | 80 | 60 | 3.58 | 2.54E+04 | 279.600 | 3.46 | 23.83 | 18.66 | 1.27 |
| E18 | CP4 | 0.0141 | MAO | 1200 | 27 | 60 | 60 | 8.47 | 2.22E+04 | 363.300 | 2.98 | 7.57 | 4.64 | 1.70 |

[1]Approximate partial pressure of ethylene
[2]Activity in g PE/(mol Ni · bar · h)
[3]Measured by $^{13}$C-NMR. Value given in number of branches per 1000 C

Example 6

In order to determine that the catalytic centres are tightly bound to the support the following experiment was set up:

In a schlenk tube with the pertinent weight of catalyst precursor CP4 in order to reach 0,015 mmol of nickel were added 15,0 ml of a 1,5 M solution of MAO in toluene. The mixture was stirred for 4 h at 70° C. Then it was carefully filtered in order to assure that the solution was free from solid particles. From the filtered solution, 10,0 ml were taken and injected in the 1,3 L polymerisation reactor with 600 ml of heptane saturated with ethylene at 4 bar and 45° C. Then the consumption of ethylene for one hour was recorded. The value of the ethylene consumption gives an idea of the amount of catalytic centres leached to the MAO solution after the 4 h period.

For comparison the same experiment was made employing:

(Comparative 1) plain silica (without ligand and/or nickel added), (Comparative 2) a non-supported and non-functionalized alpha- diimino nickel complex [N,N'-bis(2,6-dimethylphenyl)-1,4-diaza-2,3-dimethyl-1,3-butadiene nickel dibromide complex] and (Comparative 3) this same complex supported on tieated silica according to the following procedure: The silica (6,0 g) and complex N,N'-bis(2,6-dimethylphenyl)-1, 4-diaza-2,3-dimethyl-1,3-butadiene nickel dibromide (153 mg) were suspended together in 50 ml of dichloromethane. The mixture was stirred for 22 h at room temperature and then the suspension was filtered and the solid washed thoroughly with dichloromethane before being dried for 24 h under vacuum. Finally the amount of nickel in the solid was determined analytically by ICP to be 0,06% by weight.

Apart from the ethylene consumption, the colour of the resulting solution is highly indicative of the proportion of leached catalytic centres. The results are shown in the following table tion of MAO at 70° C. for one hour. The colours shown by filtrate and solid also indicate that the catalytic centres remain attached to the solid and are not leached into the MAO solution. Comparative 1 shows that a minimum consumption of ethylene is measured with the MAO solution even when no nickel centre is present. Comparative 2 gives the maximum ethylene consumption expected after treatment with MAO under the conditions of the experiment, when the entire nickel complex is in the MAO solution. Comparative 3 shows that when the non-functionalised alpha- diimino nickel complex is added to the support there are some catalytic centres which, even after the strong treatment with MAO remain occluded within the silica while other catalytic centres are leached into the solution.

What is claimed is:

1. Diimino compounds represented by the following formulae:

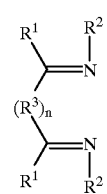

I

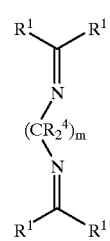

II wherein n is 0 or 1; m is 1, 2 or 3;

TABLE 3

|  | % Ni | Substrate | mmol Ni | Vol. of MAO | Al/Ni | Colour of Filtrate | Colour of Solid | Ethylene Consumption |
|---|---|---|---|---|---|---|---|---|
| Comparative 1 | 0 | 1000 mg | 0.0000 | 15.0 ml | — | Colourless | Colourless | 0.5 |
| Comparative 2 | 100 | 7.6 mg | 0.0149 | 15.0 ml | 1562 | Blue | — | 9.4 |
| Comparative 3 | 0.06 | 1468 mg | 0.0150 | 15.0 ml | 1550 | Blue | Blue | 2.6 |
| CP-4 | 0.83 | 106 mg | 0.0150 | 15.0 ml | 1550 | Colourless | Blue | 0.7 |

Table 3 shows that the catalyst CP-4 prepared according to this invention results in a catalyst system having the catalytic centres strongly attached to the support because they are not leached even after treatment with a high concentraeach $R^1$, equal to or different from each other, is selected from the group consisting of: hydrogen, a monovalent aliphatic or aromatic hydrocarbon group, optionally containing heteroatoms of group 14 to 16 of the periodic table of the elements and/or boron; with the proviso that at least one $R^1$ group is represented by the formula $R^5OSi(R)_3$;

wherein each R, equal to or different from each other, is selected from the group consisting of: $C_1-C_{20}$ alkyl, $C_3-C_{20}$ cycloalkyl, $C_6-C_{20}$ aryl, $C_2-C_{20}$ alkenyl, $C_7-C_{20}$ arylalkyl, $C_7-C_{20}$ alkylaryl, $C_8-C_{20}$ arylalkenyl, $C_8-C_{20}$ alkenylaryl;

each $R^5$, equal to or different from each other, is a divalent aliphatic or aromatic hydrocarbon group containing from 1 to 20 carbon atoms, optionally containing from 1 to 5 heteroatoms of groups 14 to 16 of the periodic table of the elements and/or boron;

each $R^2$, equal to or different from each other, is a radical which contains from 1 to 20 carbon atoms; this group optionally contains heteroatoms of group 14 to 16 of the periodic table of the elements and boron; $R^3$ is a divalent aliphatic or aromatic hydrocarbon group containing from 1 to 20 carbon atoms, optionally containing from 1 to 5 heteroatoms of groups 14, 15 and 16 of the periodic table of the elements and/or boron; each $R^4$, equal to or different from each other, is hydrogen or a radical which contains from 1 to 20 carbon atoms; this group optionally contains heteroatoms of group 14 to 16 of the periodic table of the elements and/or boron;

two or more $R^1$, $R^2$, $R^3$, $R^4$ and $R^5$ can also unite to form a 4 to 15-membered aliphatic or aromatic ring; the ring optionally contains heteroatoms of group 14 to 16 of the periodic table of the elements and/or boron.

2. Diimino compounds according to claim 1, wherein $R^5$ is represented by the formula $CR^6_2(R^7)_aCR^6_2$ wherein each $R^6$, equal to or different from each other, is selected from the group consisting of: hydrogen or R; two $R^6$ can also unite to form a ring;

$R^7$ is selected from the group consisting of: O, NR, S, $SiR^6_2$, $C_1-C_{20}$ alkylidene, $C_3-C_{20}$ cycloalkylidene, $C_2-C_{20}$ alkenylidene, $C_6-C_{20}$ arylidene, $C_7-C_{20}$ alkylarylidene, $C_7-C_{20}$ arylalkylidene, $C_8-C_{20}$ arylalkenylidene, $C_8-C_{20}$ alkenylarylidene, optionally containing heteroatoms of group 14 to 16 of the periodic table of the elements and/or boron;

a is 0 or 1.

3. Diimino compounds according to claim 2, wherein the group $CR^6_2(R^7)_aCR^6_2OSi(R)_3$ is selected from the group consisting of:

$CH_2—CH_2—OSiMe_3$, $CH_2—(CH_2)_p—CH_2—OSiMe_3$ wherein p ranges from 1 to 10, $CH_2—O—CH_2—OSiMe_3$, $CH_2—C_6H_4—CH_2—OSiMe_3$, $CH(Et)—CH_2—OSi(Et)_2Me$, $CH_2—CH_2—O—CH_2OSi(iPr)_3$, $CH_2—Si(CH_3)_2—CH_2—CH_2OSi(iPr)_3$, $CH_2—CH_2—Si(CH_3)_2—CH_2OSi(iPr)_3$, $CH_2—CH_2—CH_2—N(CH_3)—CH_2—CH_2—CH_2OSi(iPr)_3$, $C(Me)_2—CH_2—C_6H_4—CH_2—CH_2—OSi(C_5H_{11})_3$, $—CH_2—CH_2—C_6H_4—O—CH_2—CH_2—OSi(CH_2Ph)_3$, $C(CH_3)_2—C(CH_3)_2—OSi(C_6H_4Me)_3$ and $CH(Me)—CH(Me)—CH(Me)—OSi(Et)(Me)_2$.

4. Diimino compounds according to claim 1, wherein:

each $R^1$ is independently selected from the group consisting of: hydrogen, $C_1-C_{20}$ alkyl; $C_3-C_{20}$ cycloalkyl; $C_6-C_{20}$ aryl; $C_2-C_{20}$ alkenyl; $C_7-C_{20}$ arylalkyl; $C_7-C_{20}$ alkylaryl; $C_8-C_{20}$ arylalkenyl; $C_8-C_{20}$ alkenylaryl; optionally substituted by $BR^6_2$, $OR^6$, $SiR^6_3$, $NR^6_2$; or $R^5OSi(R)_3$;

each $R^2$ is independently selected from the group consisting of: $C_1-C_{20}$ alkyl, $C_3-C_{20}$ cycloalkyl, $C_6-C_{20}$ aryl, $C_2-C_{20}$ alkenyl, $C_7-C_{20}$ arylalkyl, $C_7-C_{20}$ alkylaryl, $C_8-C_{20}$ arylalkenyl, $C_8-C_{20}$ alkenylaryl, linear or branched, optionally substituted by $BR^6_2$, $OR^6$, $SiR^6_3$, $NR^6_2$;

each $R^3$ is independently selected from the group consisting of: $(CR_2)_s$ wherein s is 1 or 2, and compounds of formula:

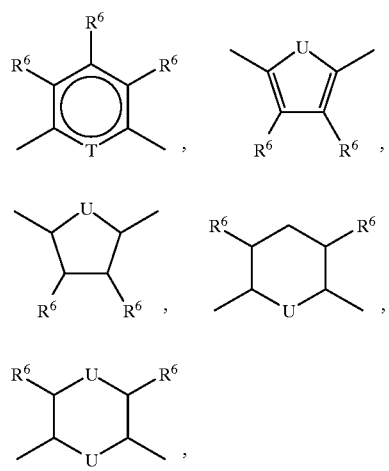

wherein

T is boron, nitrogen or phosphorus; U is boron, oxygen, nitrogen, sulphur or phosphorus;

each $R^4$ is independently selected from the group consisting of: hydrogen, $C_1-C_{20}$ alkyl, $C_3-C_{20}$ cycloalkyl, $C_6-C_{20}$ aryl, $C_2-C_{20}$ alkenyl, $C_7-C_{20}$ arylalkyl, $C_7-C_{20}$ alkylaryl, $C_8-C_{20}$ arylalkenyl, $C_8-C_{20}$ alkenylaryl, optionally substituted by $BR^6_2$, $OR^6$, $SiR^6_3$, $NR^6_2$.

5. Diimino compounds according to claim 1 represented by the following formulae:

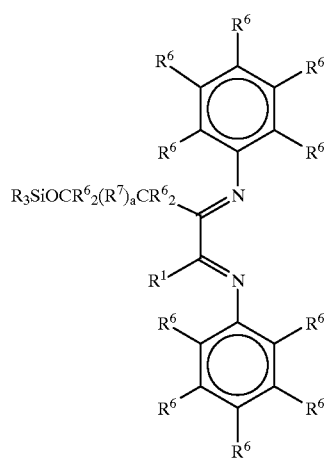

-continued

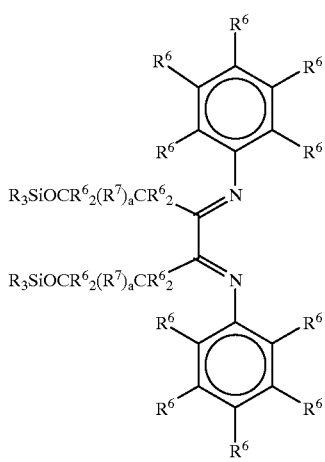

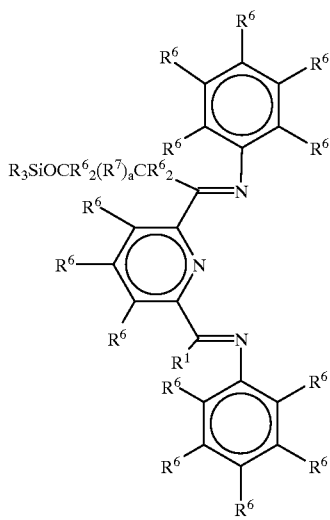

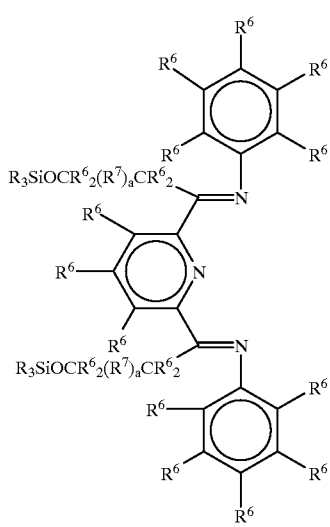

-continued

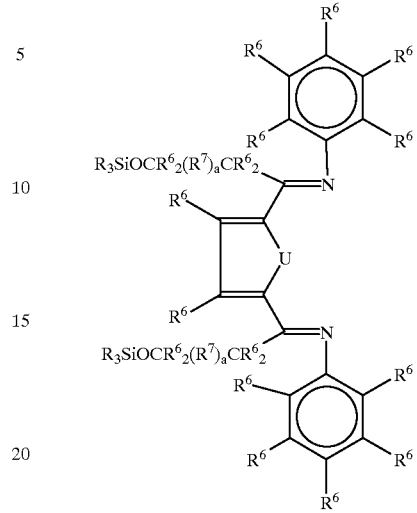

6. A process for the preparation of diimino compounds comprising:

a) reacting a compound of general formulas III or IV

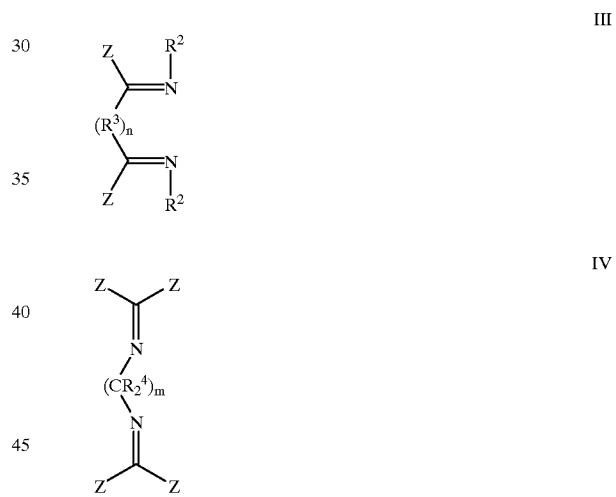

with a Bronsted base selected from the group consisting of: organolithium compounds, organosodium compounds, organopotassium compounds, organomagnesium compounds, sodium hydride, potassium hydride, lithium, sodium, or potassium;

b) contacting the obtained metallated compound with one equivalent of a compound of general formula $Y(R^7)_a CR^6{}_2OSi(R)_3$ wherein n is 0 or 1; m is 1, 2 or 3;

each Z is independently selected from the group consisting of: $R^1$ and $CR^6{}_2H$, provided that at least one Z is represented by the formula $CR^6{}_2H$, each $R^1$ equal to or different from each other, is selected from the group consisting of: hydrogen, a monovalent aliphatic or aromatic hydrocarbon group, optionally containing heteroatoms of group 14 to 16 of the periodic table of the elements and/or boron;

each R, equal to or different from each other, is selected from the group consisting of: $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalk $C_7$–$C_{20}$ alkylaryl, $C_8$–$C_{20}$ arylalkenyl, $C_8$–$C_{20}$ alkenylaryl;

each $R^2$, equal to or different from each other, is a radical which contains from 1 to 20 carbon atoms; this group optionally contains heteroatoms of group 14 to 16 of the periodic table of the elements and boron;

$R^3$ is a divalent aliphatic or aromatic hydrocarbon group containing from 1 to 20 carbon atoms, optionally containing from 1 to 5 heteroatoms of groups 14, 15 and 16 of the periodic table of the elements and/or boron;

each $R^4$, equal to or different from each other, is hydrogen or a radical which contains from 1 to 20 carbon atoms; this group optionally contains heteroatoms of group 14 to 16 of the periodic table of the elements and/or boron;

two or more $R^1$, $R^2$, $R^3$, $R^4$ and $R^5$ can also unite to form a 4 to 15-membered aliphatic or aromatic ring; the ring optionally contains heteroatoms of group 14 to 16 of the periodic table of the elements and/or boron;

each $R^6$, equal to or different from each other, is selected from the group consisting of: hydrogen or R, wherein R is as defined above; two $R^6$ can also unite to form a ring;

$R^7$ is selected from the group consisting of: O, NR, S, $SiR^6_2$, $C_1$–$C_{20}$ alkylidene, $C_3$–$C_{20}$ cycloalkylidene, $C_2$–$C_{20}$ alkenylidene, $C_6$–$C_{20}$ arylidene, $C_7$–$C_{20}$ alkylarylidene, $C_7$–$C_{20}$ arylalkylidene, $C_8$–$C_{20}$ arylalkenylidene, $C_8$–$C_{20}$ alkenylarylidene, optionally containing heteroatoms of group 14 to 16 of the periodic table of the elements and/or boron;

a is 0 or 1;

Y is a leaving group.

7. The process for the preparation of diimino ligand of claim 6, wherein the Bronsted base is selected from the group consisting of lithium alkyl, sodium alkyl, polassium alkyl; and Y is halogen.

8. Solid catalyst component for polymerizing olefins obtainable by a process comprising the following steps:

a) reacting a dilmino ligand according to claim 1, with a porous inorganic support;

b) treating the reaction mixture with a compound of general formula $L_qMX_2$, wherein M is selected from the group 8, 9 and 10 of the periodic table, each X, equal to or different from each other, is selected from a group consisting of: halogen, hydrogen, OR, $N(R)_2$, $C_1$–$C_{20}$ alkyl or $C_6$–$C_{20}$ aryl; two X taken together can also be an aromatic or aliphatic divalent ligand, containing two equal or different donor atoms belonging to the group 14–16 of the periodic table of the elements; L is a labile ligand and q is 0, 1 or 2; each R, equal to or different from each other, is selected from the group consisting of: $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ aylalkenyl, $C_8$–$C_{20}$ alkenylaryl.

9. The catalyst component of claim 8, wherein the porous inorganic solid is selected from the group consisting of: silica, alumina, silica-alumina, aluminum phosphates and mixtures thereof.

10. The catalyst component of claim 8, wherein the porous inorganic solid is calcined silica.

11. A polymerization catalyst comprising a cocatalyst and a catalyst component for polymerizing olefins obtained by a process comprising the following steps:

a) reacting a diimino ligand according to claim 1, with a porous inorganic support;

b) treating the reaction mixture with a compound of general formula $L_qMX_2$, wherein M is selected from the group 8, 9 and 10 of the periodic table, each X, equal to or different from each other, is selected from a group consisting of: halogen, hydrogen, OR, $N(R)_2$, $C_1$–$C_{20}$ alkyl or $C_6$–$C_{20}$ aryl; two X taken together can also be an aromatic or aliphatic divalent ligand, containing two equal or different donor atoms belonging to the group 14–16 of the periodic table of the elements; L is a labile ligand and q is 0, 1 or 2; each R, equal to or different from each other, is selected from the group consisting of: $C_1$–$C_{20}$ alky, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, $C_8$–$C_{20}$ alkenylaryl.

12. The polymerization catalyst of claim 11, wherein the cocatalyst is selected from the group consisting of: aluminoxane, boron compound, or mixtures thereof.

13. A polymerization process comprising contacting one or more olefms with a catalyst system comprising a cocatalyst and a catalyst component for polymerizing olefms obtained by a process comprising the following steps:

a) reacting a diimino ligand according to claim 1, with a porous inorganic support;

b) treating the reaction mixture with a compound of general formula $L_qMX_2$, wherein M is selected from the group 8, 9 and 10 of the periodic table, each X, equal to or different from each other, is selected from a group consisting of: halogen, hydrogen, OR, $N(R)_2$, $C_1$–$C_{20}$ alkyl or $C_6$–$C_{20}$ aryl; two X taken together can also be an aromatic or aliphatic divalent ligand, containing two equal or different donor atoms belonging to the group 14–16 of the periodic table of the elements; L is a labile ligand and q is 0, 1 or 2; each R, equal to or different from each other, is selected from the group consisting of: $C_1$–$C_{20}$ alkyl, $C_3$–$C_{20}$ cyclolkyl, $C_6$–$C_{20}$ aryl, $C_2$–$C_{20}$ alkenyl, $C_7$–$C_{20}$ arylallyl, $C_7$–$C_{20}$ alkylaryl, $C_8$–$C_{20}$ arylalkenyl, $C_8$–$C_{20}$ alkenylaryl.

14. eopolymerization process of claim 13 wherein the olefin is ethylene.

15. The polymerization process of claim 13 wherein the olefin are ethylene and one or more of butene, hexene, octene, 4-methylpentene.

* * * * *